United States Patent
Lin et al.

(10) Patent No.: US 6,344,276 B1
(45) Date of Patent: Feb. 5, 2002

(54) NON-DISSOLVABLE AMORPHOUS TI-CA-P COATING FOR IMPLANT APPLICATION

(75) Inventors: Jiin-Huey Chern Lin, No. 18, Lane 725, Chiu Ju 4 Rd., Ku Shan District, Kaohsiung; Chien-Ping Ju, Room 607, No. 350, Tung Feng Rd., Tainan; Shinn-Jyh Ding, Taipei, all of (TW)

(73) Assignees: Jiin-Huey Chern Lin, Kaohsiung; Chien-Ping Ju, Tainan, both of (TW)

( * ) Notice: Subject to any disclaimer, the term of this patent is extended or adjusted under 35 U.S.C. 154(b) by 0 days.

(21) Appl. No.: 09/314,155

(22) Filed: May 19, 1999

(51) Int. Cl.[7] .......................... B32B 15/04; A61C 13/00
(52) U.S. Cl. ........................ 428/469; 428/472; 428/689; 428/702; 433/201.1
(58) Field of Search ................................. 428/469, 472, 428/472.1, 689, 693, 701, 702, 548, 555, 615, 660; 106/35, 287.19, 287.23, 287.29; 433/201.1, 203.1, 222.1; 623/23.53, 23.55, 23.56, 23.57, 23.6, 11.11

(56) References Cited

U.S. PATENT DOCUMENTS

| | | | | |
|---|---|---|---|---|
| 5,330,826 A | * | 7/1994 | Taylor et al. | |
| 5,342,199 A | * | 8/1994 | Gillespie | |
| 5,543,019 A | * | 8/1996 | Lee et al. | |
| 5,817,326 A | * | 10/1998 | Nastasi et al. | |
| 6,013,591 A | * | 1/2000 | Ying et al. | |

* cited by examiner

Primary Examiner—Deborah Jones
Assistant Examiner—Jennifer McNeil
(74) Attorney, Agent, or Firm—Bacon & Thomas

(57) ABSTRACT

A medical implant coated with an amorphous hydroxyapatite/titanium coating layer having both high coating-substrate bond strength and a low dissolution rate of the coating. The medical implant of the present invention includes a substrate and a surface coating deposited onto the substrate from a composite target comprising 10–75% by volume of titanium and 90–25% by volume of hydroxyapatite.

14 Claims, 25 Drawing Sheets

NON-DISSOLVABLE AMORPHOUS TI-CA-P COATING FOR IMPLANT APPLICATION

BACKGROUND OF THE INVENTION

1. Field of the Invention

The present invention relates to medical implants. More particularly, the present invention relates to a medical implant with a non-dissolvable amorphous hydroxyapatite/titanium coating.

2. Description of the Related Art

Over the past fifteen years or so, much effort has been made to develop calcium phosphate-based coatings on metallic substrate, such as commercially pure Ti (c.p. Ti), Ti alloys (typically Ti—6Al–4V), Co–Cr alloys and stainless steel, for the application of a variety of load-bearing medical implants. The most popular coating among the entire calcium phosphate family was hydroxyapatite (HA) due to its chemical stability and osteoconductivity. The most promising metallic system for implant application were found to be Ti and its alloys due to their biocompatibility and mechanical properties.

Important parameters in the long-term behavior of implants coated with HA include at least high coating-substrate bond strength and a low dissolution rate of the coating. In order to improve coating-substrate (usually a metal) bond strength and other properties, a variety of coating techniques have been explored to develop thin (generally less than 10 $\mu$m) coatings of HA and other calcium phosphates. U.S. Pat. No. 4,908,030, "Method of Manufacturing Synthetic Bone Coated Surgical Implants," discloses a method of forming a thin HA coating on an implant using ion beam sputtering. U.S. Pat. No. 5,817,326, "Processing of Hydroxylapatite Coatings on Titanium Alloy Bone Prostheses," discloses a method in which one or more layers of HA sol-gel are cured to densify on a titanium alloy implant, followed by a non-line-of-sight ion implantation process, in order to strengthen the adhesion of the HA coating to the substrate. U.S. Pat. No. 5,543,019, "Method of Coating Medical Devices and Device Coated Thereby," discloses a method of forming a thin coating layer on the surface of an implant using a plasma sputtering process. Other methods developed include pulsed laser deposition and magnetron sputtering.

Another approach to improve the bonding capability of HA coating onto metallic substrate has been the deposition of a composite coating, wherein a metallic phase is introduced to serve as either an intermediate layer or a second (continuous or dispersed) phase in HA matrix. For example, Dasarathy et al., in "Hydroxyapatite/metal composite coatings formed by electrocodeposition," *J. Biomed. Mater. Res.*, 31, 81–89 (1996), applied an electro-codeposition process to coat a Co/HA composite coating on Ti substrate with a bond strength up to 37 MPa. Using plasma spray technique, Brossa et al., in "Adhesion properties of plasma sprayed hydroxyapatite coatings for orthopaedic prostheses," *Bio-Med. Mater. Eng.*, 3, 127–136 (1993), and Nakashima et al., in "Hydroxyapatite coating on titanium-sprayed titanium implant," in *Bioceramics* 6, P. Ducheyne and D. Christiansen (eds.), Butterworth-Heinemann, Oxford, 1993, pp. 449–453, applied a double-layer comprising an HA layer on top of a porous Ti precoat on a Ti substrate. This double-layered coating was shown to outperform monolithic HA coating in adhesion properties. In German patent "Coating of implants," Gruner, Heiko (Plasmainevent A.-G.) Ger. Offen. DE 3,516,411 (Cl. C23C4/04) Nov. 12, 1986, Gruner teaches a multi-layered coating comprising a Ti precoat, a Ti/HA composite layer and an HA overlayer by plasma deposition. The multi-layer coated implants show fast and stable fusion between the coated implant and the bone. On Ti—6Al—4V substrate Ferraris et al., in "Vacuum plasma spray deposition of titanium particle/glass-ceramic matrix biocomposites," *J. Am. Ceram. Soc.*, 79, 1515–1520 (1996), plasma-sprayed a Ti particle-reinforced bioactive glass composite coating, which exhibited a higher bond strength than that of monolithic bioactive glass coating.

Concerning the dissolution rate of HA coating, much effort has been made on the study of immersion behavior of HA coating in simulated body fluid (SBF). This in vitro study is practically important, since it could be some indication of in vivo behavior of the coating, especially when thin coatings are pursued. During immersion tests, unfortunately, many thin HA coatings are extensively dissolved in short periods of time. For example, using an ion beam dynamic mixing technique Ohtsuka et al., in "Formation of hydroxyapatite coating on pure titanium substrates by ion beam dynamic mixing," *Surface Coating Technol.*, 65, 224–230 (1994), have developed an amorphous HA coating. However, this amorphous film dissolved almost completely within 1 day in Hanks' solution without further annealing. Ong et al., in , "Structure, solubility and bond strength of thin calcium phosphate coatings produced by ion beam sputter deposition," *Biomaterials*, 13, 249–254 (1992), found that a thin (<1 $\mu$m) amorphous calcium phosphate coating could be deposited by ion beam sputtering. Nevertheless, this film was also dissolved completely within a few hours in saline solution. Wolke et al., "In vivo dissolution behavior of various RF magnetron sputter Ca—P coatings," *J. Biomed. Mater. Res.*, 39, 524–530 (1998), used radio frequency (RF) magnetron-assisted sputtering technique to deposit on titanium substrate thin (<10 $\mu$m) films of amorphous HA. Again, these amorphous coatings were dissolved when implanted subcutaneously into the back of rabbits.

SUMMARY OF THE INVENTION

It is therefore an object of the present invention to provide a medical implant coated with a single amorphous hydroxyapatite layer having both high coating-substrate bond strength and a low dissolution rate of the coating.

The present invention achieves the above described object by providing a medical implant with an non-dissolvable amorphous hydroyapatite/titanium coating. The medical implant with a non-dissolvable amorphous hydroyapatite/titanium coating of the present invention comprises: a substrate, and a surface coating deposited onto the substrate from a composite target comprising 10–75 % by volume of titanium and 90–25% by volume of hydroxyapatite, preferably comprising 10–50% by volume of titanium and 90–50 % by volume of hydroxyapatite. The substrate can be comprised of pure titanium or a titanium alloy, for example Ti—6Al—4V. The surface coating can be less than approximately 10 $\mu$m thick. The hydroxyapatite component of the composite target can be calcinated. The weight ratio of Ca+P to titanium in the surface coating is in the range of approximately 0.1–3.0, preferably 0.4–3.0.

The present invention further provides a method for producing a medical implant having a non-dissolvable amorphous hydroxyapatite/titanium coating, comprising the steps of: fabricating a substrate; fabricating a composite target comprising 10–75 % by volume of titanium and 90–25 % by volume of hydroxyapatite; and depositing the composite target onto the substrate to form a surface coating thereupon by using an ion sputtering technique, a laser ablation technique, or a physical vapor deposition technique. An additional step of calcinating the hydroxyapatite can be performed before the step of fabricating the composite target.

The medical implant coated with a amorphous hydroyapatite/titanium coating layer of the present invention offers the advantages of both high coating-substrate bond strength and a low dissolution rate of the coating in simulated body fluid, making it suitable for application in dental implants, orthopedic prosthesis, and other types of medical implants.

BRIEF DESCRIPTION OF DRAWINGS

The following detailed description, given by way of examples and not intended to limit the invention to the embodiments described herein, will best be understood in conjunction with the accompanying drawings, in which.

DETAILED DESCRIPTION OF THE INVENTION

Figure 1:
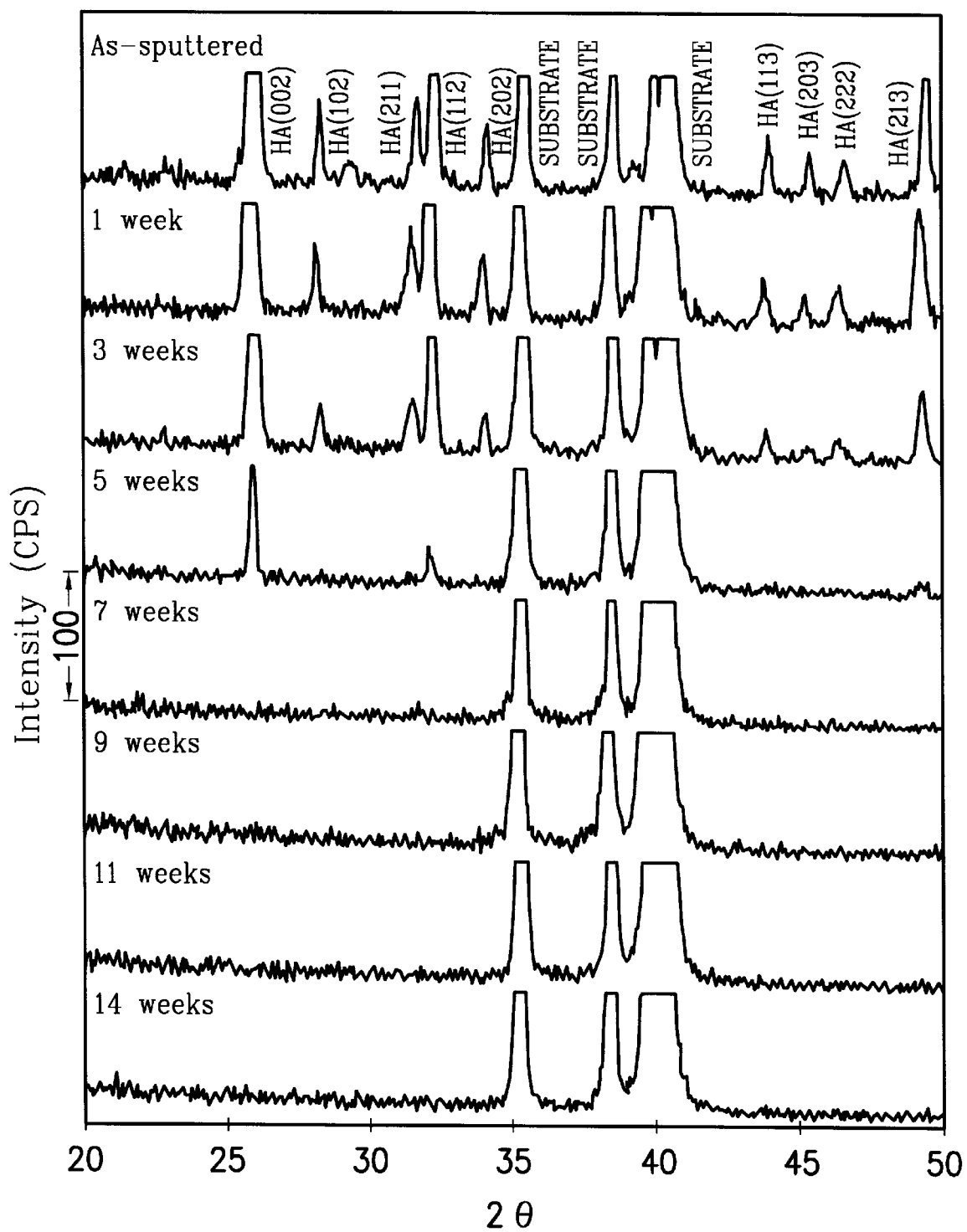
FIGS. 1–8 illustrate the XRD patterns for various as-sputtered and immersed coatings over different immersion times.

A preferred mode of practicing the invention is given as follows. In the following examples, commercially available 3 mm thick Ti—6Al—4V plates were used as the substrate of the medical implant. However, it is to be understood that the substrate can be, for example, a dental implant, an orthopedic prosthesis, or another type of medical implant. Further, the implant could be comprised of pure titanium or one of its alloys. The substrate surface was mechanically polished to a roughness of Ra=0.06 $\mu$m, where Ra is average roughness. Prior to sputtering, the polished substrate surface was etched in 30% $HNO_3$ for 30 min, followed by ultrasonic cleaning in acetone for 10 min.

To fabricate HA/Ti composite targets, appropriate amounts of HA and Ti powders were mixed in ethanol in a ball mill pot for 24 h. A commercial HA powder (Merck A. G., Darmstadt, Germany) calcinated at 900° C. for 3 h was used. The Ti was a commercially pure (99.5%) Ti powder with particle size less than 44 $\mu$m (Kojundo Chemical Laboratory, Osaka, Japan). After drying, the HA/Ti mixture was cold-pressed in a 7.6 cm dia. stainless steel mold under a pressure of 50 MPa to obtain 3 mm thick HA/Ti composite targets. For simplicity, all the composite targets (or coatings from the same) are designated "xHA/yTi", where x and y stand for the volume fractions of HA and Ti in the targets, respectively. Six HA/Ti targets with different compositions (95HA/5Ti, 90HA/10Ti, 85HA/15Ti, 75HA/25Ti, 50HA/50Ti and 25HA/75Ti) were prepared. Monolithic HA and Ti targets were also fabricated for the sake of comparison.

The sputter chamber was evacuated to a base pressure lower than $10^{-5}$ torr, then back-filled with high purity (99.9995%) argon until a working pressure of $10^{-2}$ torr was obtained. Prior to deposition, the substrate surface was first sputter-cleaned for 10 min at 1 kV DC bias. The target was also sputter-cleaned to remove surface contaminant as well as activate the surface of the target. The magnetron-assisted sputter deposition was proceeded using a RF generator operated at 300 W with a frequency of 13.56 MHz (RF5S, RF Plasma Products, Kresson, N.J. USA). The distance between target and substrate was fixed at 5 cm. The as-sputtered thicknesses of the series of coatings are listed in Table I.

TABLE I

As-Sputtered Coating Thickness and Deposition Time

| Coating Code | Target Composition HA:TI | | Coating Thickness ($\mu$m) | Deposition Time (h) at 300 W |
| --- | --- | --- | --- | --- |
| | Vol. Ratio | Wt. Ratio | | |
| HA | 100:0 | 100:0 | 3 | 6 |
| 95HA/5Ti | 95:5 | 13:1 | 4 | 6 |
| 90HA/10Ti | 90:10 | 6:1 | 6 | 5.5 |
| 85HA/15Ti | 85:15 | 4:1 | 7 | 5 |
| 75HA/25Ti | 75:25 | 2:1 | 6 | 4 |
| 50HA/50Ti | 50:50 | 2:3 | 6 | 3 |
| 25HA/75Ti | 27:75 | 2:9 | 4.5 | 2 |
| Ti | 0:100 | 0:100 | 3 | 1 |

EXPERIMENTS

A variety of synthetic solutions, such as tris-buffer and Hanks' physiological solutions, have often been used for in-vitro biodegradation/bioactivity evaluation. The simulated body fluid (SBF) suggested by Kukobo was used for all immersion tests described herein (Table II). The solution was buffered to pH 7.4 with 50 mM trishydroxymethyl aminomethane (($CH_2OH)_3CNH_2$) and 45 mM hydrochloric acid (HCl). The coated specimens, each with a surface area of 1 $cm^2$, were immersed in vials containing 20 ml of SBF, and were maintained at 37° C. throughout tests. The solution was agitated daily by hand to help maintain uniform ion concentrations.

After certain predetermined periods of time, the specimens were removed from the vials and examined using a low vacuum scanning electron microscope (Topcon SM-300, Tokyo, Japan). Using this low vacuum SEM (LVSEM), specimens could be examined under a "wet" condition and the conventional deposition of a conducting film was not needed, thus largely eliminating a variety of difficulties such as high vacuum and charging-induced structural damage. The specimens for cross-sectional examination were prepared by mechanical polishing to a level of 1 $\mu$m $Al_2O_3$ powder following the standard metallographic procedure.

Phases of the various coatings were identified using an X-ray diffractometer (Rigaku D-MAX IIB, Tokyo, Japan) with Ni-filtered Cuk☐ radiation operated at 30 kV and 20 mA at a scanning speed of 1°/min. A Fourier transform infrared spectroscopy (FTIR) system (Bomem DA8.3, Hartman & Braun, Canada) in reflection absorption mode with a spectral resolution of 2 $cm^1$ was used to characterize the various functional groups on the coating surface. Adhesion strengths of the various coatings were measured using a commercial Sebastian system (Sebastian Five, Quad Group, Spokane, Wash. USA). In doing the testing, a 2.7 mm dia. aluminum pull stud was bonded to the coated surface with an epoxy, that was then cured at 150° C. for 1 h in oven. After the sputtered specimen/stud assembly was gripped on a platen, the stud was then pulled down against the platen until failure occurred.

A field emission scanning electron microscope (SEM) (Hitachi S-4200, Hitachi, Tokyo, Japan) equipped with an energy dispersive spectroscopy (EDS) system (Noran Instrument Inc., Middleton, Wis. USA) was used for microstructural and chemical analyses of the various coatings.

TABLE II

Composition of Simulated Body Fluid Used in Experiments

| Constituent | g/L |
| --- | --- |
| NaCl | 7.9949 |
| NaHCO$_3$ | 0.3528 |
| KCl | 0.2235 |
| K$_2$HPO$_4$ | 0.1470 |
| MgCl$_2$.6H$_2$O | 0.3050 |
| CaCl$_2$ | 0.2775 |
| Na$_2$SO$_4$ | 0.710 |

RESULTS

X-ray diffraction

The X-ray diffraction (XRD) patterns of sputtered specimens (monolithic HA, 95HA/5Ti, 90HA/10Ti, 85HA/15Ti, 75HA/25Ti, 50HA/50Ti, 25HA/75Ti, and monolithic Ti) immersed in SBF for different periods of time are respectively shown in FIGS. 1–8. As indicated in FIG. 1, the as-sputtered monolithic HA coating was highly crystalline with a strong (002) preferred orientation. After immersion in SBF, however, this 3 μm thick HA coating was gradually dissolved. The 7-week XRD pattern did not show any apatite peak, indicating the monolithic HA coating was entirely dissolved in SBF in 7 weeks.

Figure 2:
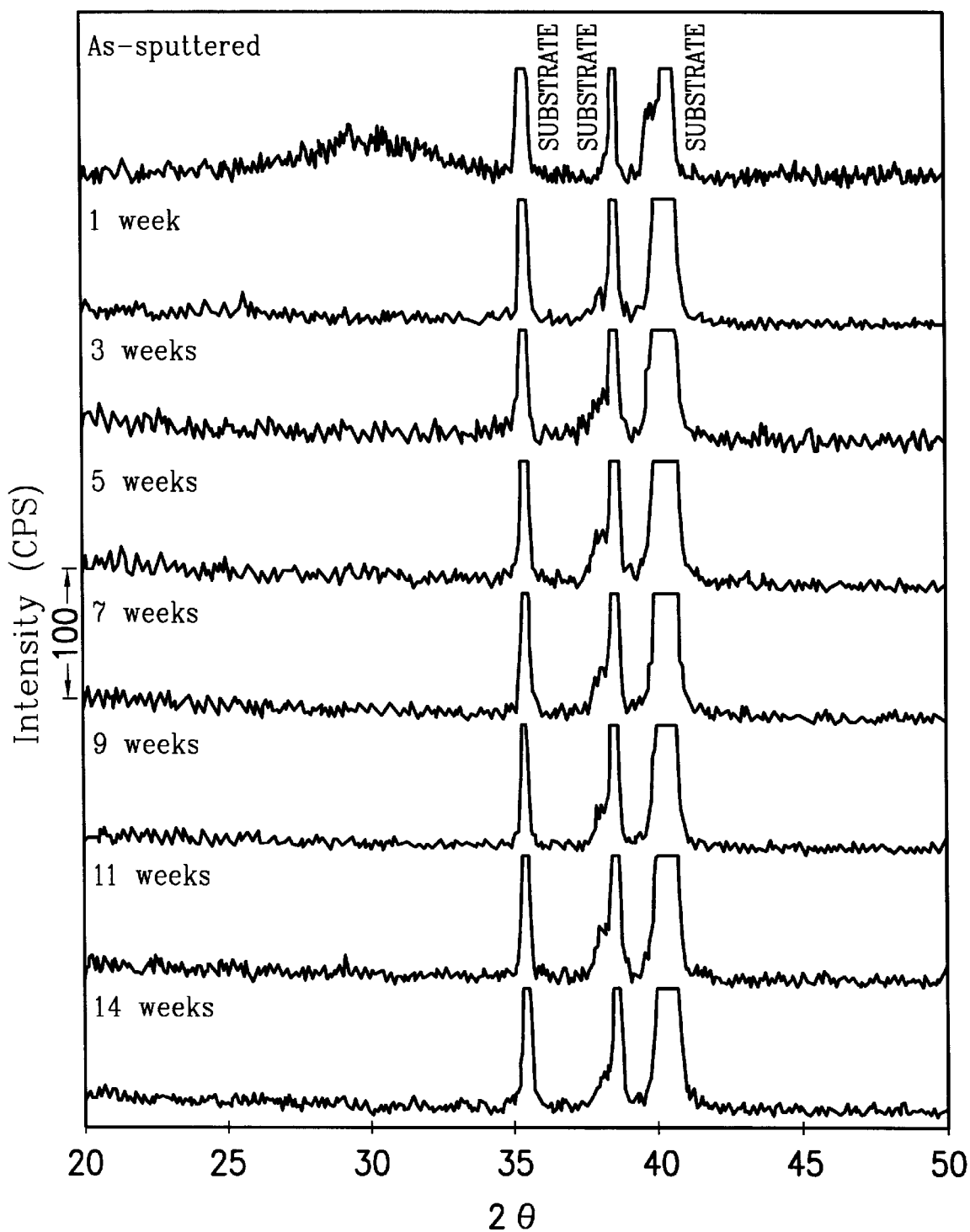

When 5 vol % Ti was mixed into the target (95HA/5Ti), the XRD pattern of the resulting coating showed a broad and diffuse peak roughly between 25 and 35°, the most intensive diffraction angle for apatite, as shown in FIG. 2. This indicates that the highly crystalline structure observed in monolithic HA coating could be largely disrupted through the mixing of Ti of even a small amount in the coating. This broad peak largely disappeared after 1 week of immersion, indicating that the thin (4 μm) coating was either severely dissolved or delaminated from substrate in SBF in a week.

Figure 3:
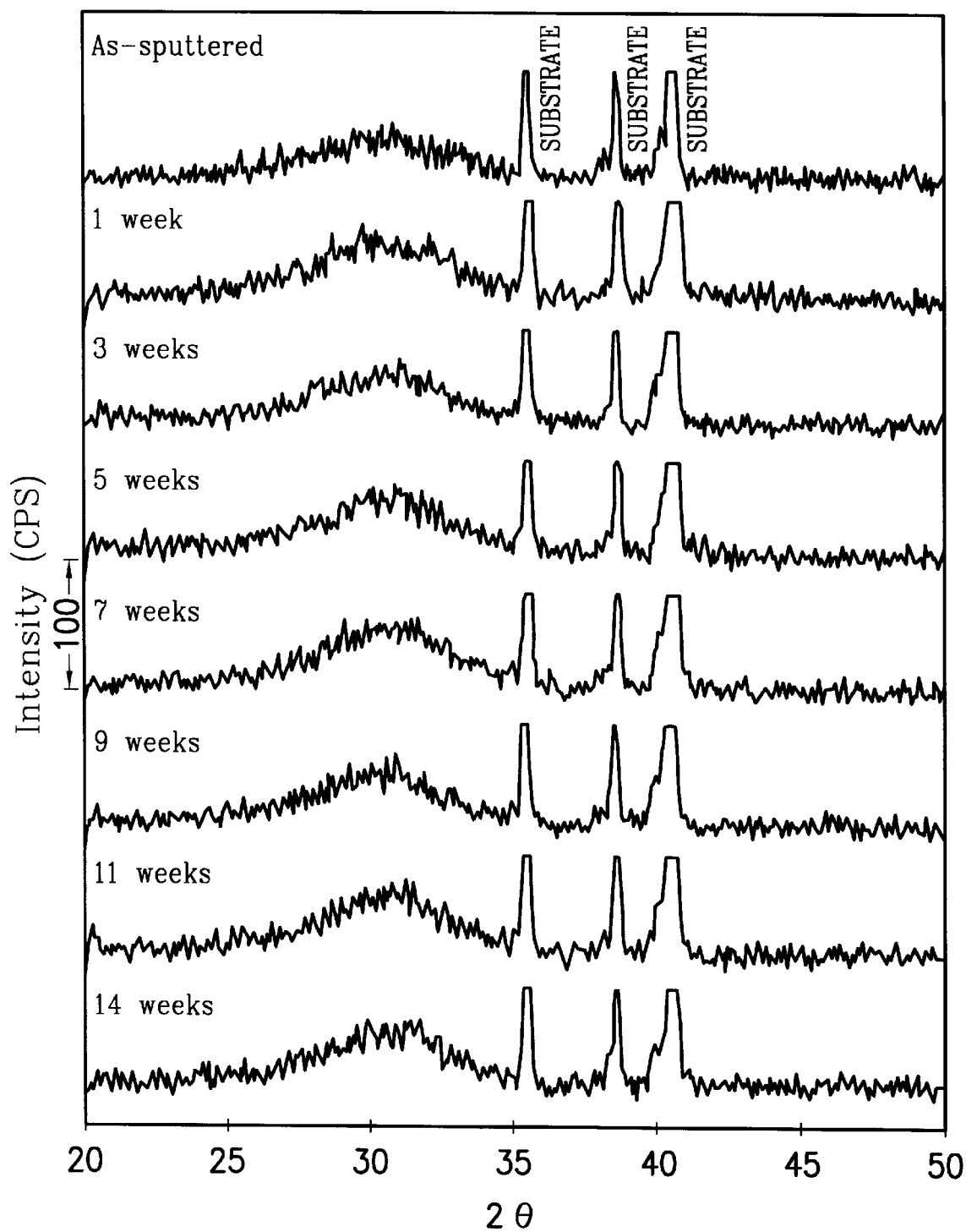
Figure 4:
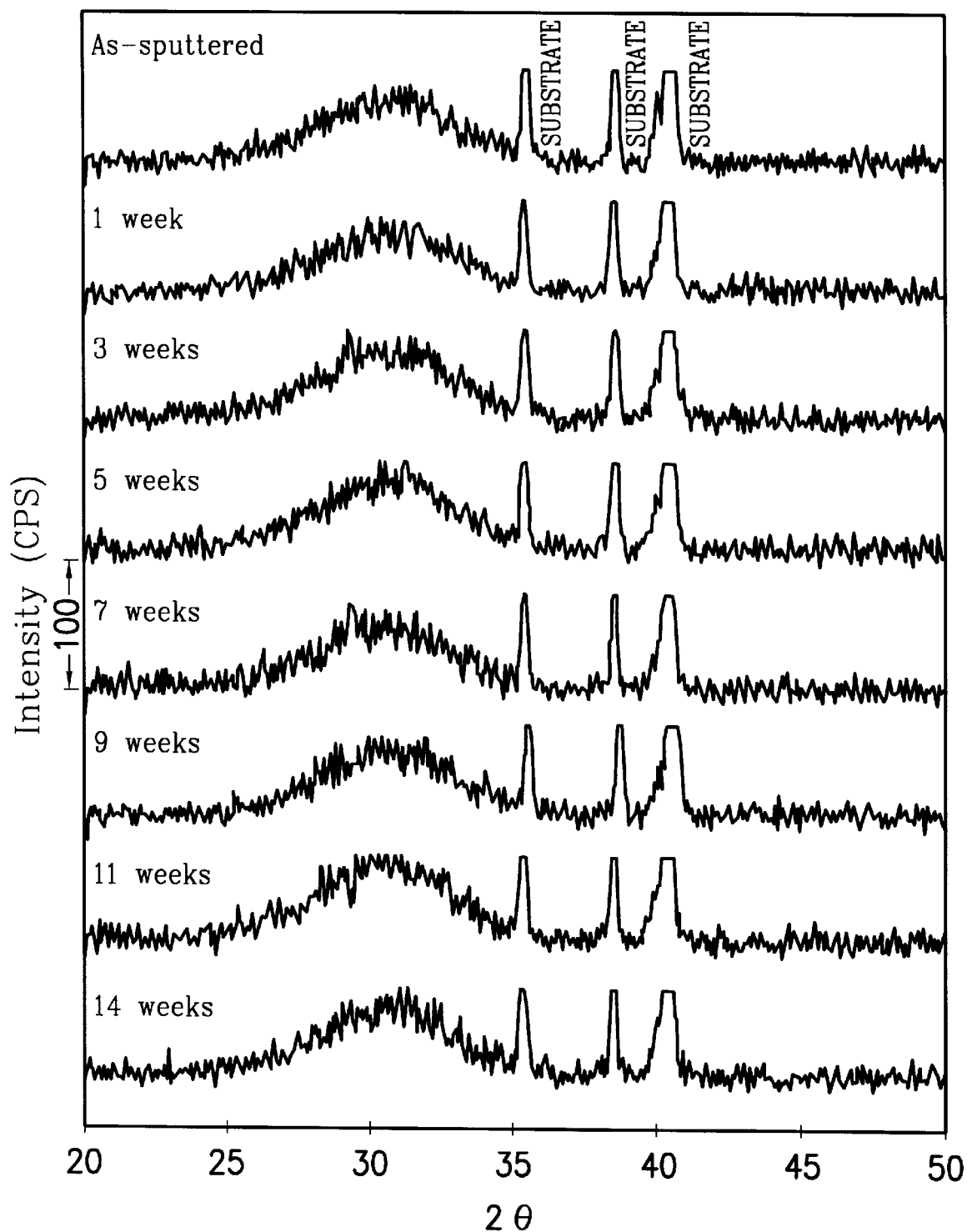
Figure 5:
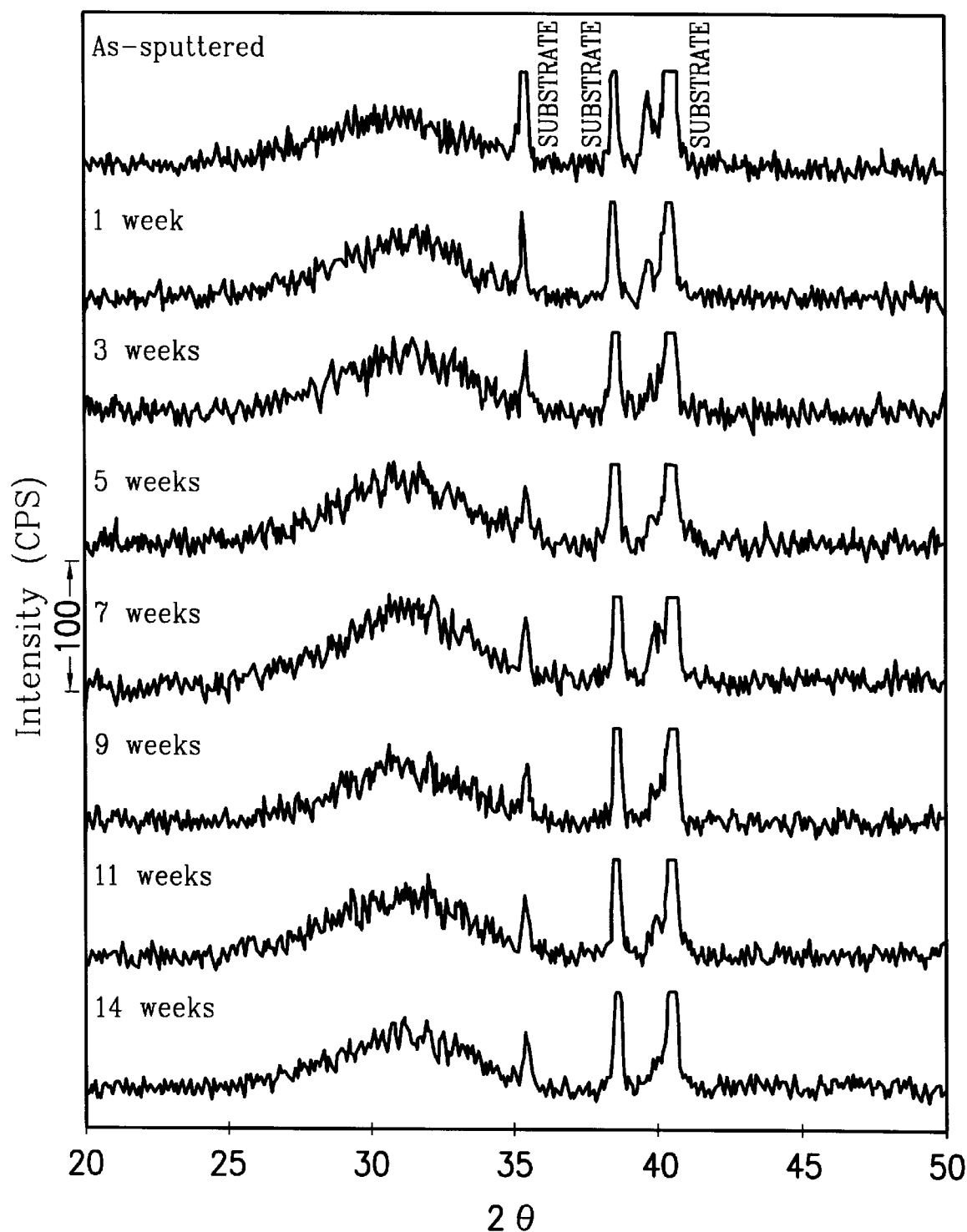

The as-sputtered 90HA/10Ti coating showed a similar amorphous-like structure, but remarkably different immersion behavior from that of 95HA/5Ti coating. The broad peak of apatite between 25 and 35° remained similar throughout the immersion test (up to 14 weeks), as shown in FIG. 3. The XRD patterns of as-sputtered and immersed 85HA/15Ti and 75HA/25Ti (FIGS. 4–5) were both similar to that of 90HA/10Ti.

Figure 6:
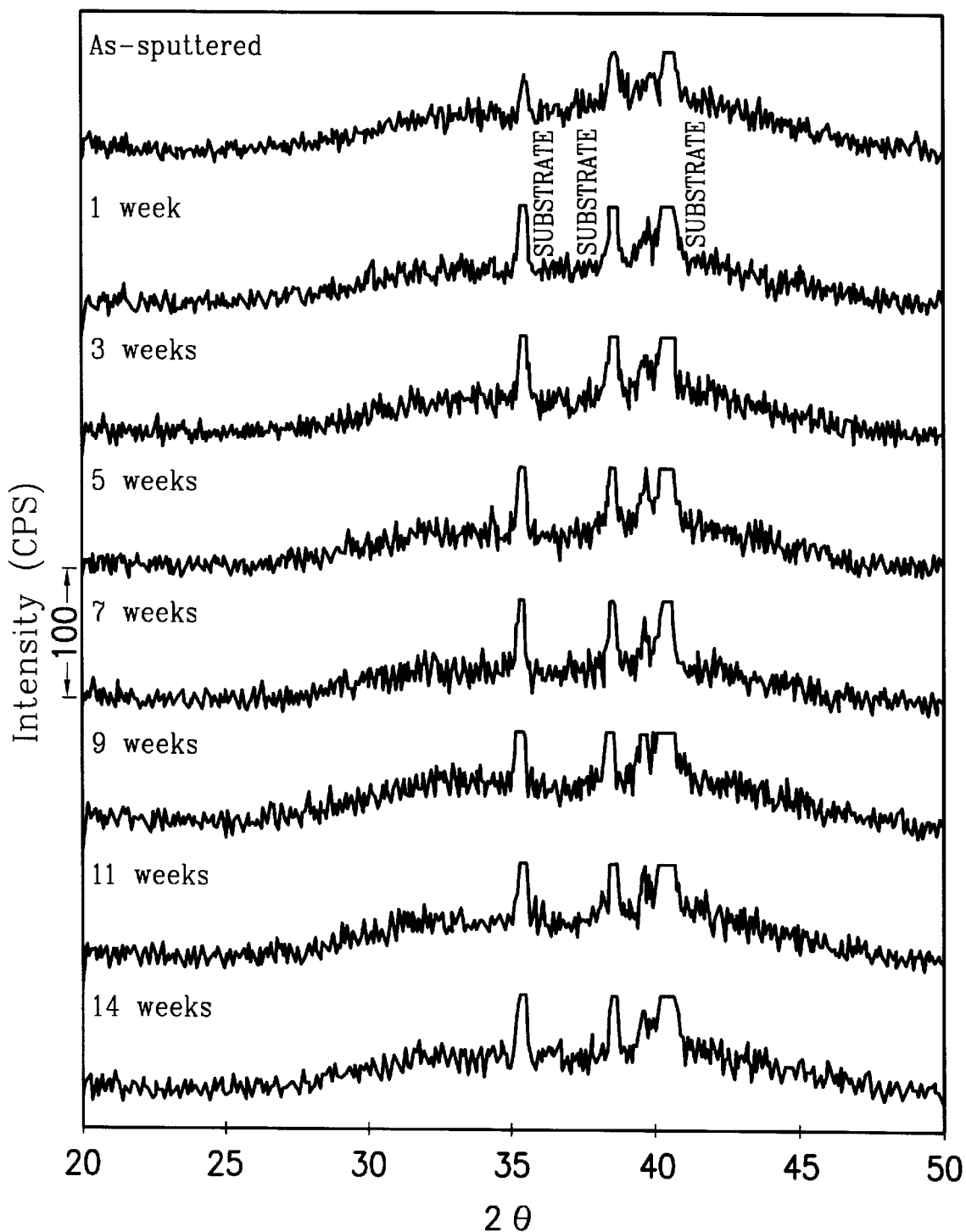
Figure 7:
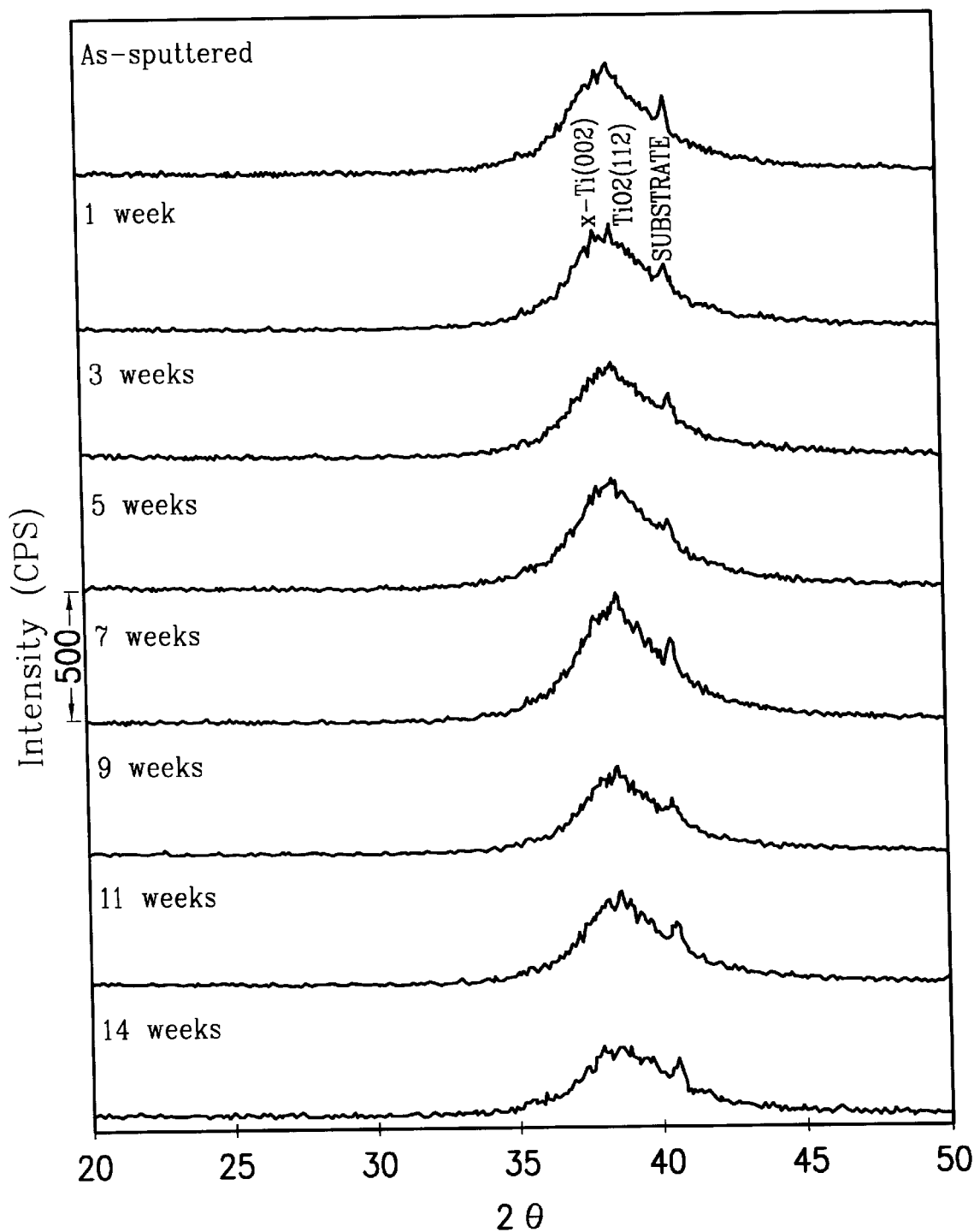
Figure 8:
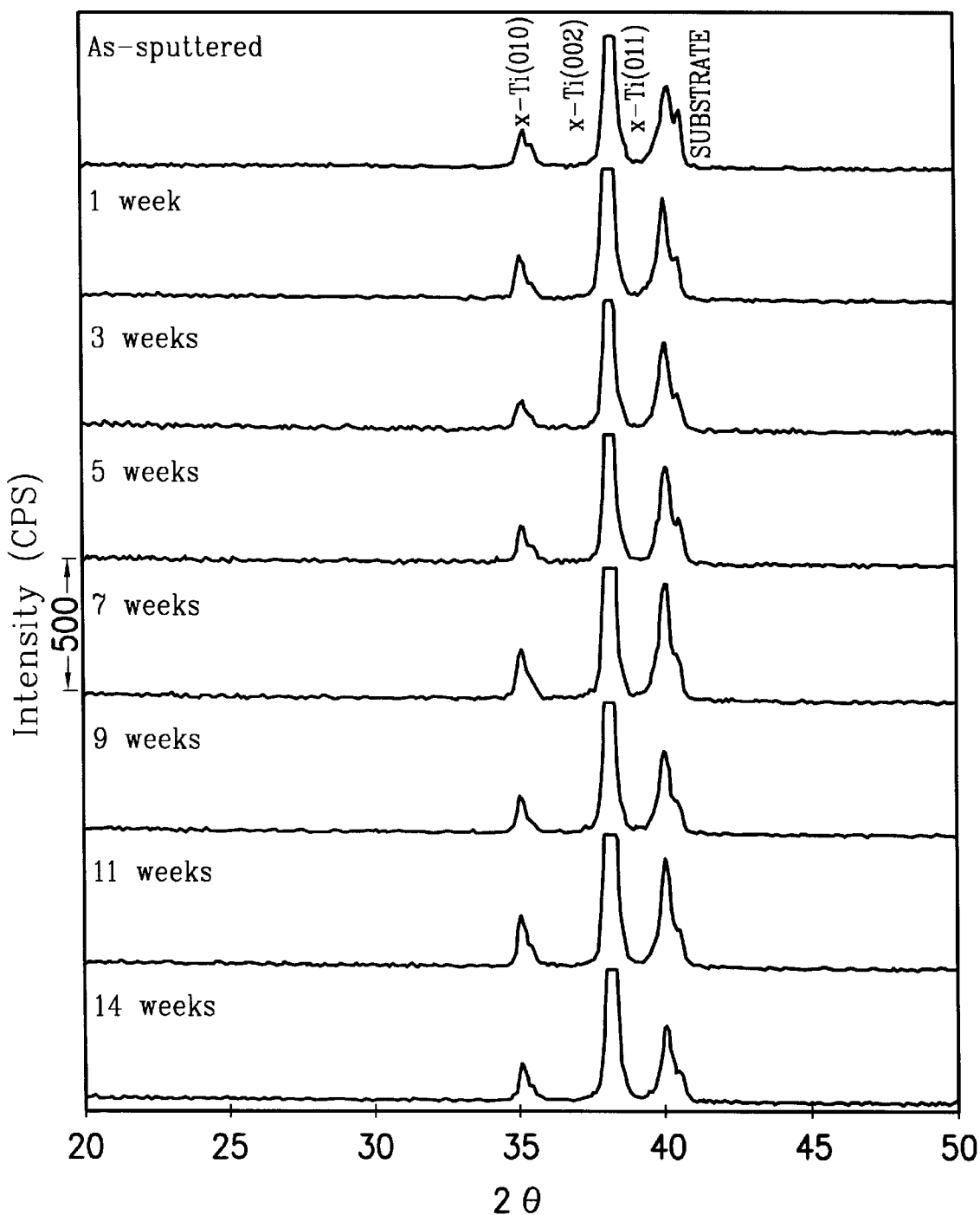

When the target contained 50 vol % Ti, the diffuse peak of apatite (25–35°) became weaker and the diffuse peak of Ti roughly between 35 and 45° (the most intensive diffraction angle of Ti) became more significant, as shown in FIG. 6. Like 90HA/10Ti, 85HA/15Ti and 75HA/25Ti, the XRD patterns of 50HA/50Ti did not change with immersion time. As Ti content was further increased to 75 vol %, the entire XRD pattern of as-sputtered coating became dominated by a single broad peak of Ti due to the much higher sputter yield of Ti than HA, as shown in FIG. 7. Again, the XRD patterns of 25HA/75Ti remained similar throughout immersion test. The XRD pattern of as-sputtered monolithic Ti showed a typical highly crystalline structure. Due to its relatively large thickness, the XRD peaks shown in FIG. 8 were predominantly from the coating rather than substrate.

From the present XRD results, it can be seen that if Ti content was higher than 10 vol % in the target, the resulting coating became non-dissolvable in SBF throughout the immersion test. When the target comprised 75 vol % Ti or more, the entire coating became predominantly composed of Ti.

Fourier transform infrared spectroscopy

Figure 9:
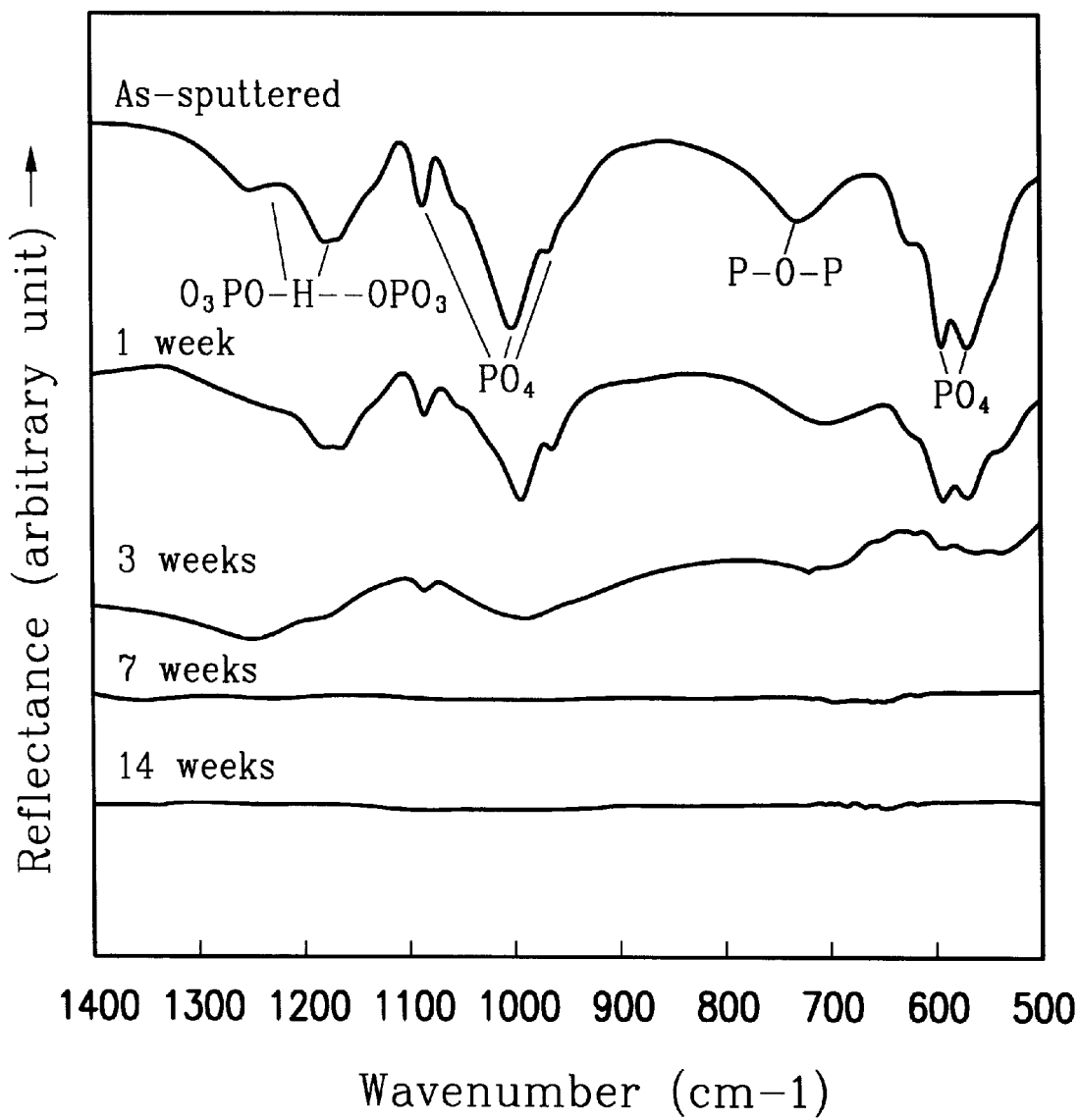
FIGS. 9–16 illustrate the FTIR spectra for various as-sputtered and immersed coatings over different immersion times.

The as-sputtered monolithic HA coating exhibited many absorption bands in its FTIR reflection spectrum attributed to various functional groups, as shown in FIG. 9. The sharp bands at 1081, 1001, 964, 592 and 568 cm$^{-1}$ in the spectrum were attributed to PO$_4$ functional group. The peaks at 1250 and 1178 cm$^{-1}$ were suggested to arise from the in-plane bending modes of interphosphate or hydrogen-bonded OH among (O$_3$PO—H—OPO$_3$) group. The absorption band at 730 cm$^{-1}$ was possibly attributed to the librational vibration mode of P—O—P chain. The weak band at 625 cm$^{-1}$, which was derived from the vibrational modes of OH-, indicated the presence of a dehydroxylated HA structure. The sharpness of the FTIR profile of monolithic HA coating indicated that the dehydroxylated HA structure was highly crystallized, in agreement with the earlier XRD result.

When immersed in SBF, the intensities of all absorption bands of monolithic HA coating continued to decrease with time, as shown in FIG. 9, indicating that the immersed coating was experiencing a dissolution/degradation process. After 3 weeks, intensities of all the bands became very low. After 7 weeks, all bands virtually disappeared, indicating that the coating was either entirely dissolved or detached from the Ti—6Al—4V substrate with no characteristic absorption bands. This FTIR result is consistent with the earlier XRD result (FIG. 1).

The FTIR spectrum of as-sputtered 95HA/5Ti coating (FIG. 10) was significantly different from that of as-sputtered monolithic HA coating. The strong peaks at 1001, 592 and 568 cm$^{-1}$ that appeared in the spectrum of monolithic HA coating became weak, while the bands at 1161, 970 and 764–642 cm$^{-1}$ were significant. The general broadening of FTIR bands was a direct indication that the structure of the coating became less ordered, consistent with the XRD result (FIG. 2). After immersion for 1 week, the band intensities at 1160, 970, and 764–642 cm$^{-1}$ (HPO$_4$ and/or PO$_4$ groups) decreased significantly. After 3 weeks, the entire FTIR profile became featureless, indicating that the coating was completely dissolved or detached. It was difficult, from the XRD pattern, to trace the small amount of residue of 95HA/5Ti coating immersed for 1 week, yet this small amount of coating residue was easily recognized by FTIR due to its smaller penetration depth.

Figure 11:
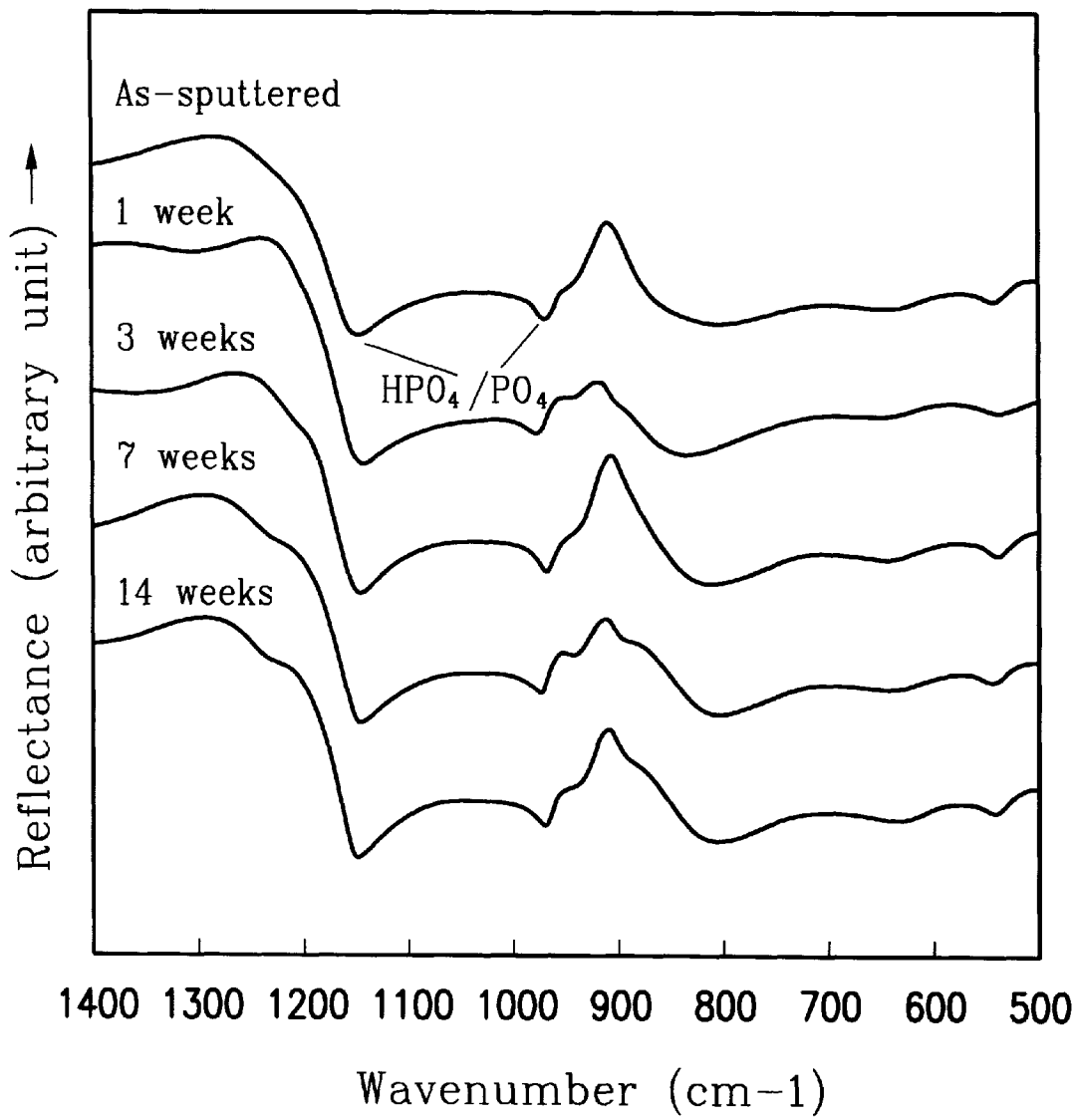
Figure 12:
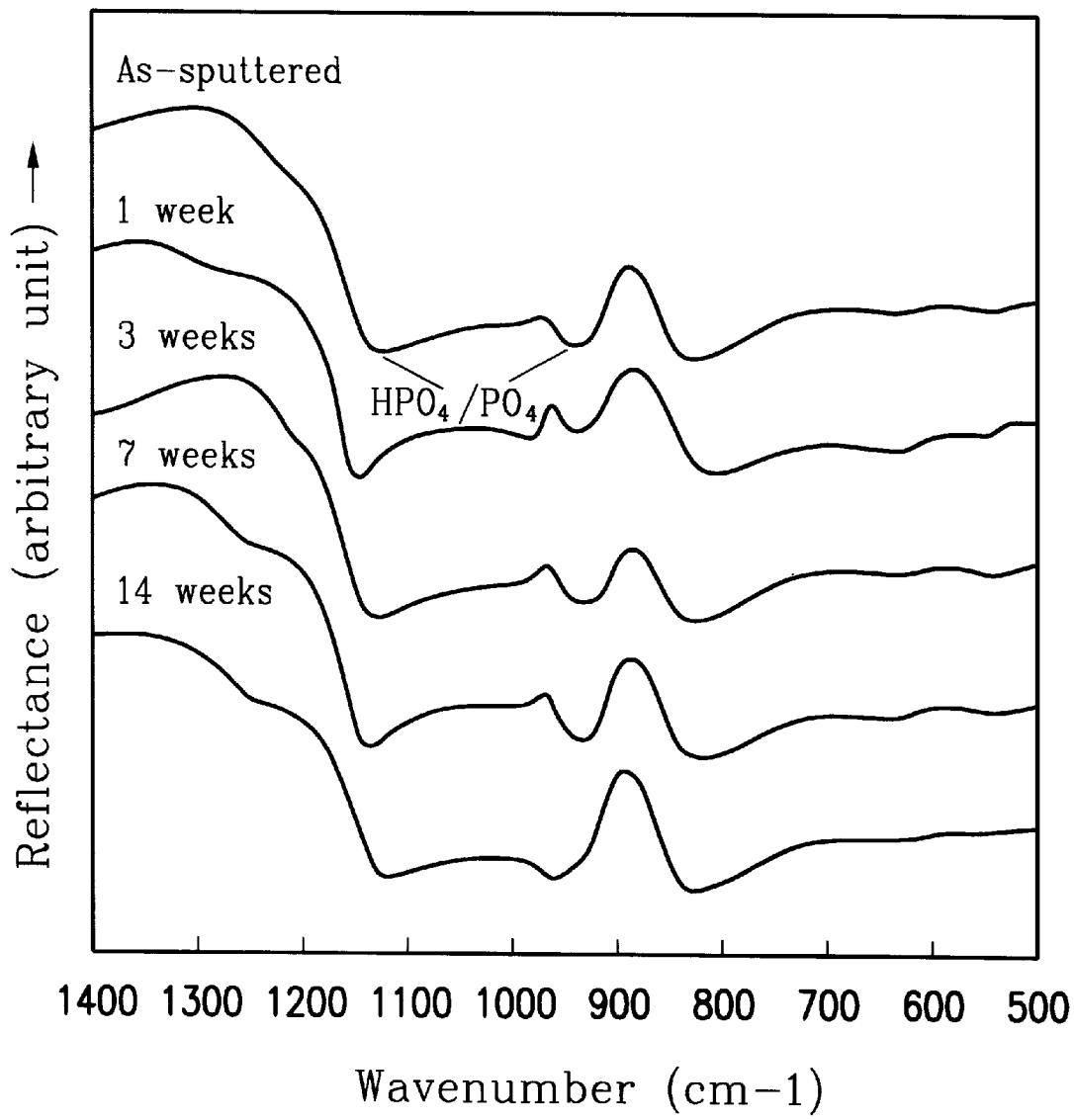
Figure 13:
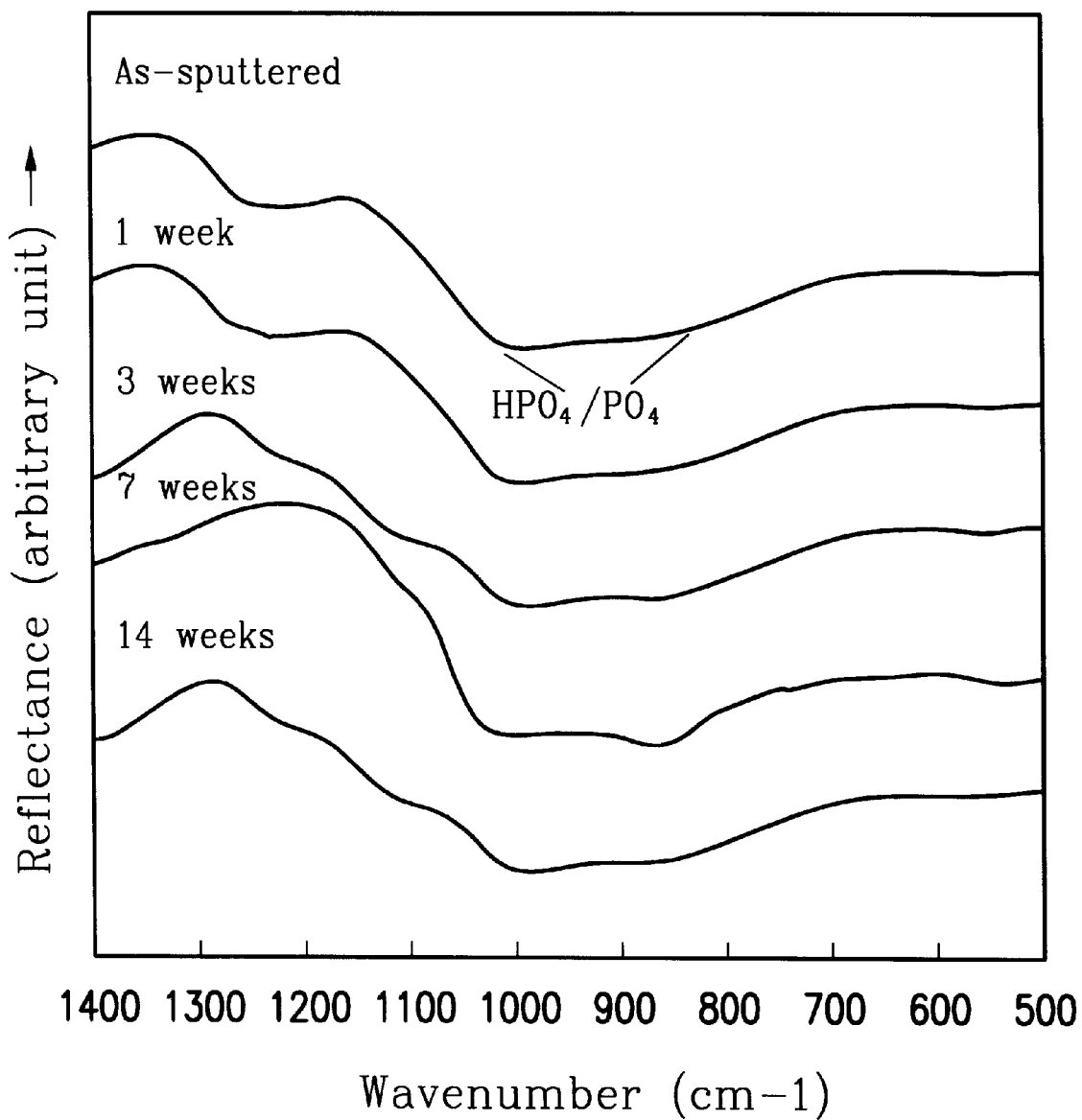
Figure 14:
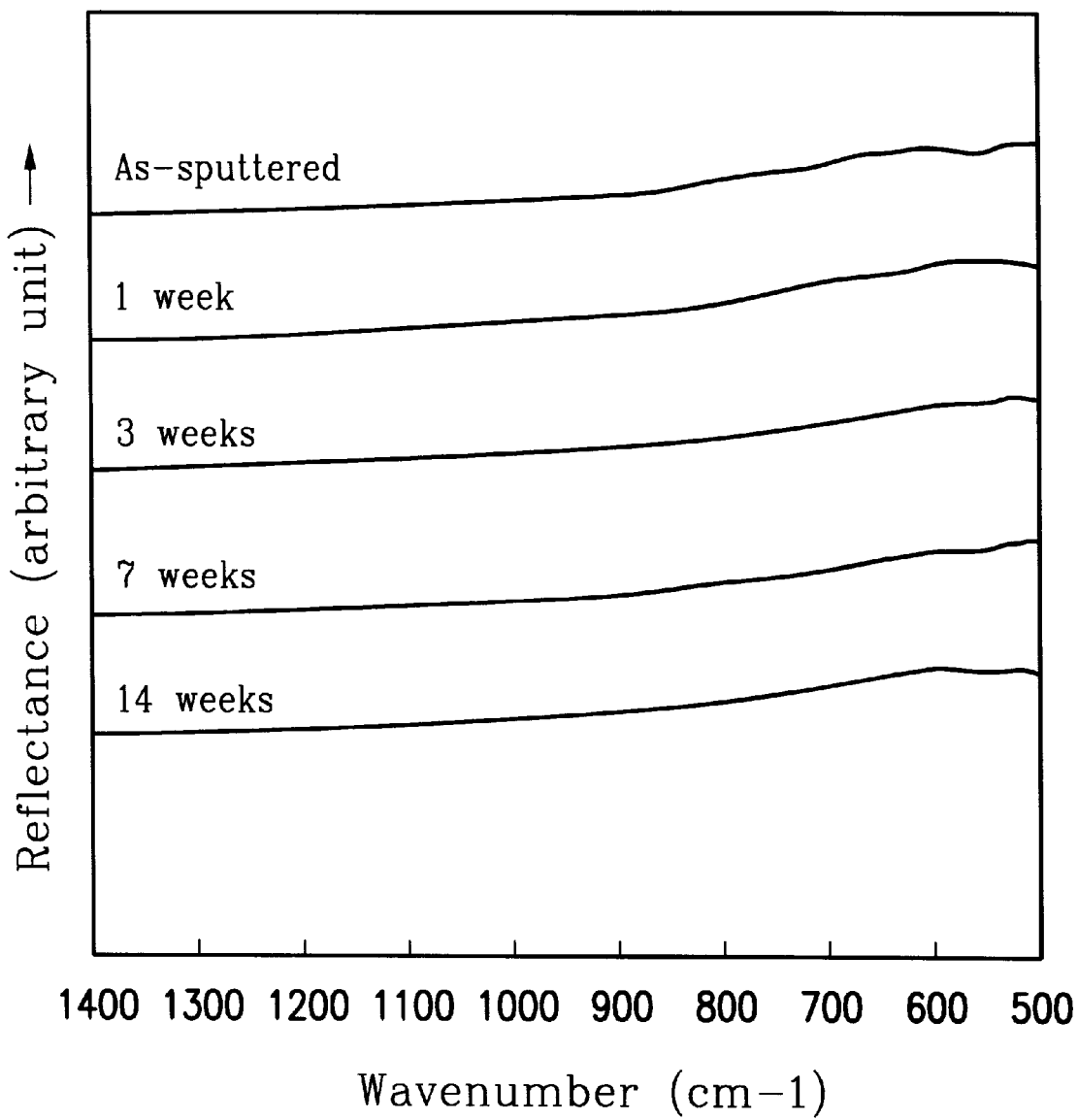
Figure 15:
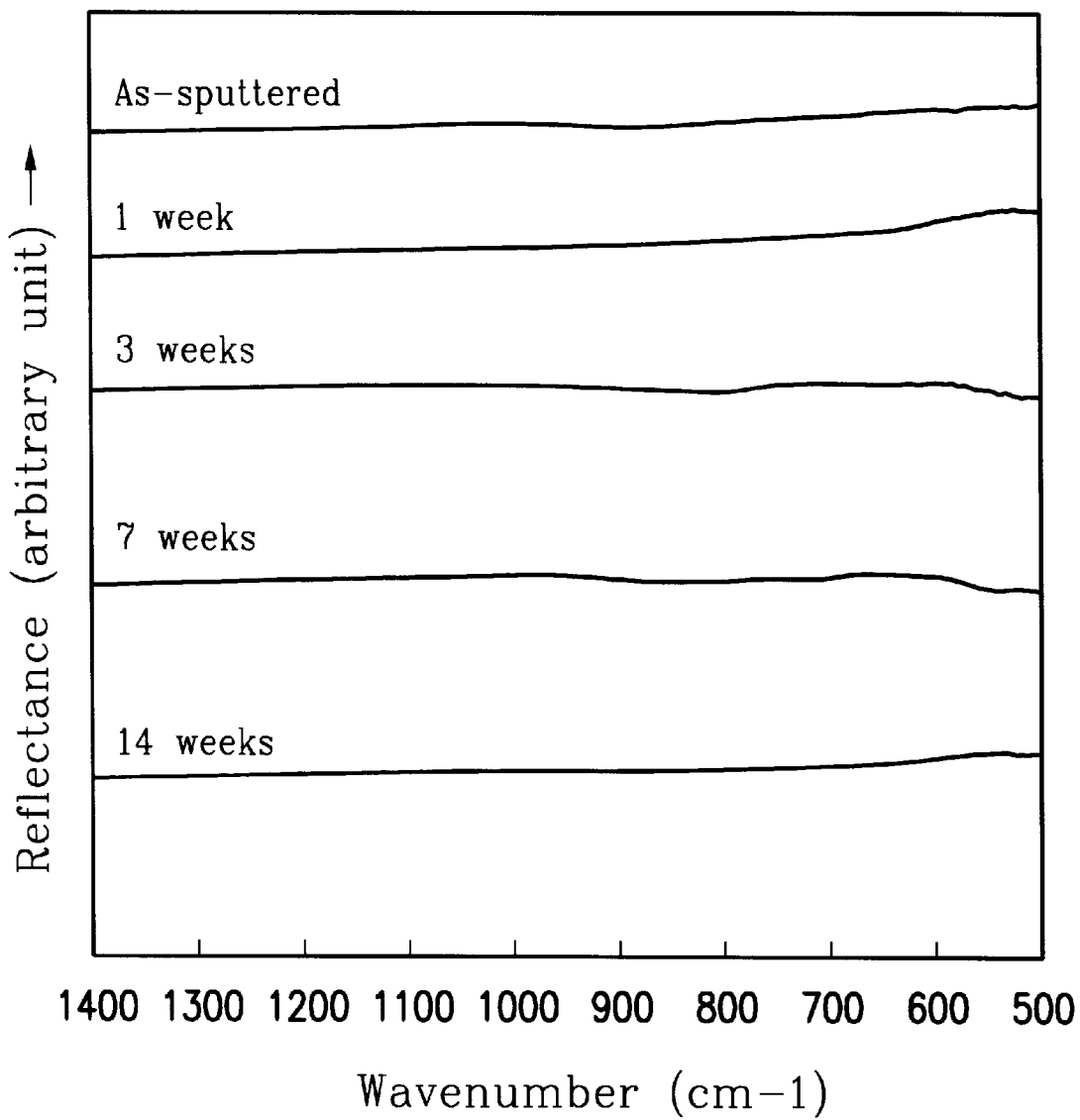
Figure 16:
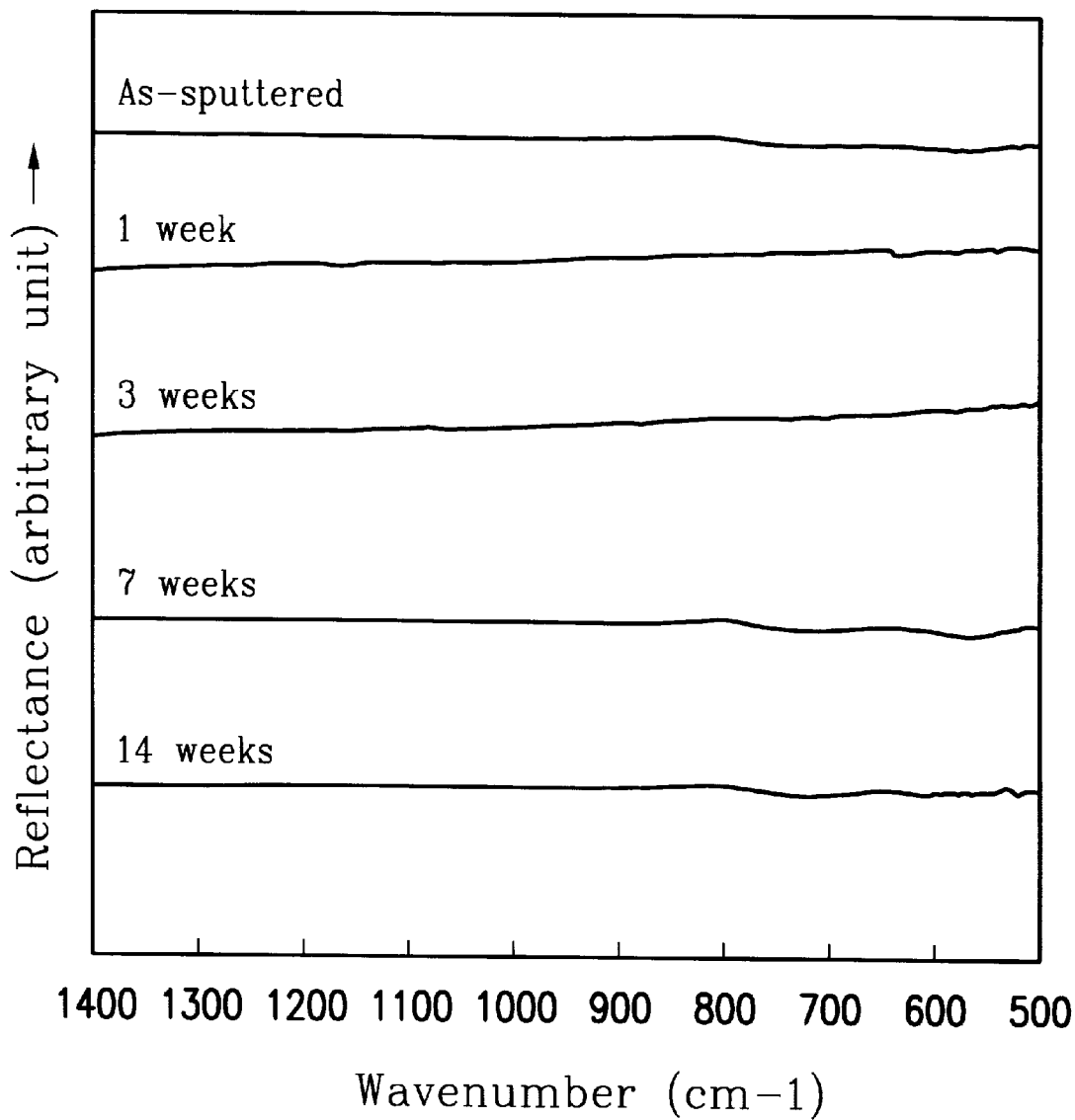
Figure 17:
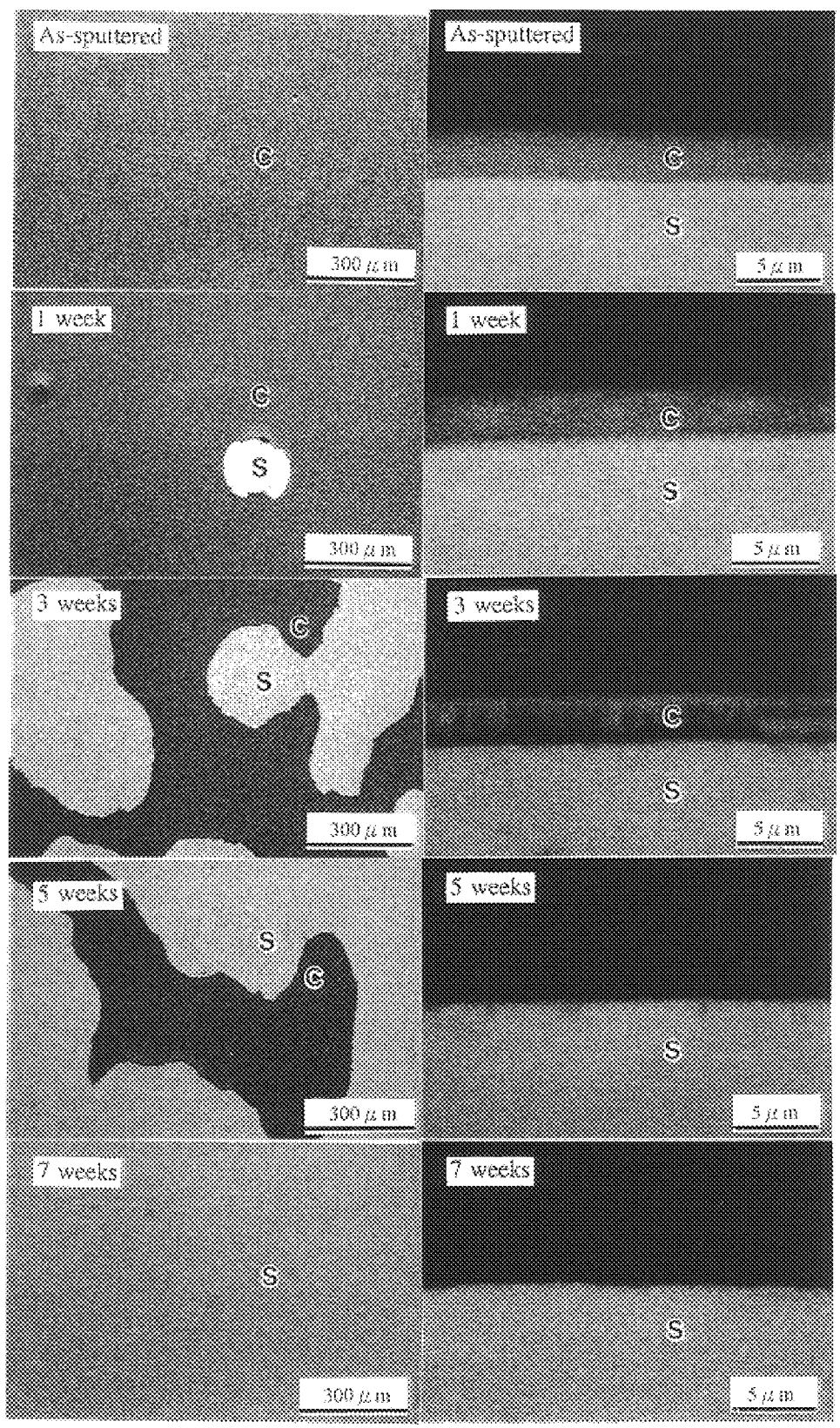
FIGS. 17–24 illustrate the LVSEM micrographs for various as-sputtered and immersed coatings over different immersion times.

The FTIR spectra of 90HA/10Ti (FIG. 11) and 85HA/15Ti (FIG. 12) coatings were similar, except that the peaks at 980 and 1150 cm$^{-1}$ in the spectrum of 85HA/15Ti coating were flatter and the peaks at 943 and 903 cm$^{-1}$ observed in 90HA/10Ti were combined into a broad band in the spectrum of 85HA/15Ti coating. The spectrum of 75HA/25Ti coating (FIG. 13) became even broader between 850 and 1060 cm$^{-1}$, indicating that the degree of crystallinity of the coatings further decreased. When targets were comprised of 50 vol % or more Ti, the FTIR spectra became featureless (FIG. 14), indicating that the coatings were predominantly composed of Ti, consistent with the XRD esults.

From bioactivity-enhancing point of view, it is referable that the volume fraction of Ti in the target should be less than 50%. As can be seen from FIGS. 11–16, when targets comprising 10 vol % or more Ti were sputtered, the FTIR spectra of the resulting coatings did not change significantly throughout immersion tests, in agreement with the earlier XRD results.

Coating morphology

Variations in broad face and cross-sectional morphology of the series of coatings immersed in SBF are shown in FIGS. 17–24. As shown in the low vacuum SEM micrographs (FIG. 17), the monolithic HA coating started to separate locally from the substrate as early as in the first week of immersion. After 3 weeks, a large portion of the coating has spalled off the substrate. The 7-week micrographs showed that the entire coating has peeled off. These SEM micrographs clearly showed that the delamination, rather than a uniform dissolution, of the coating was the major reason for the earlier-observed fast decrease in XRD and FTIR intensities of apatite phase.

Figure 10:
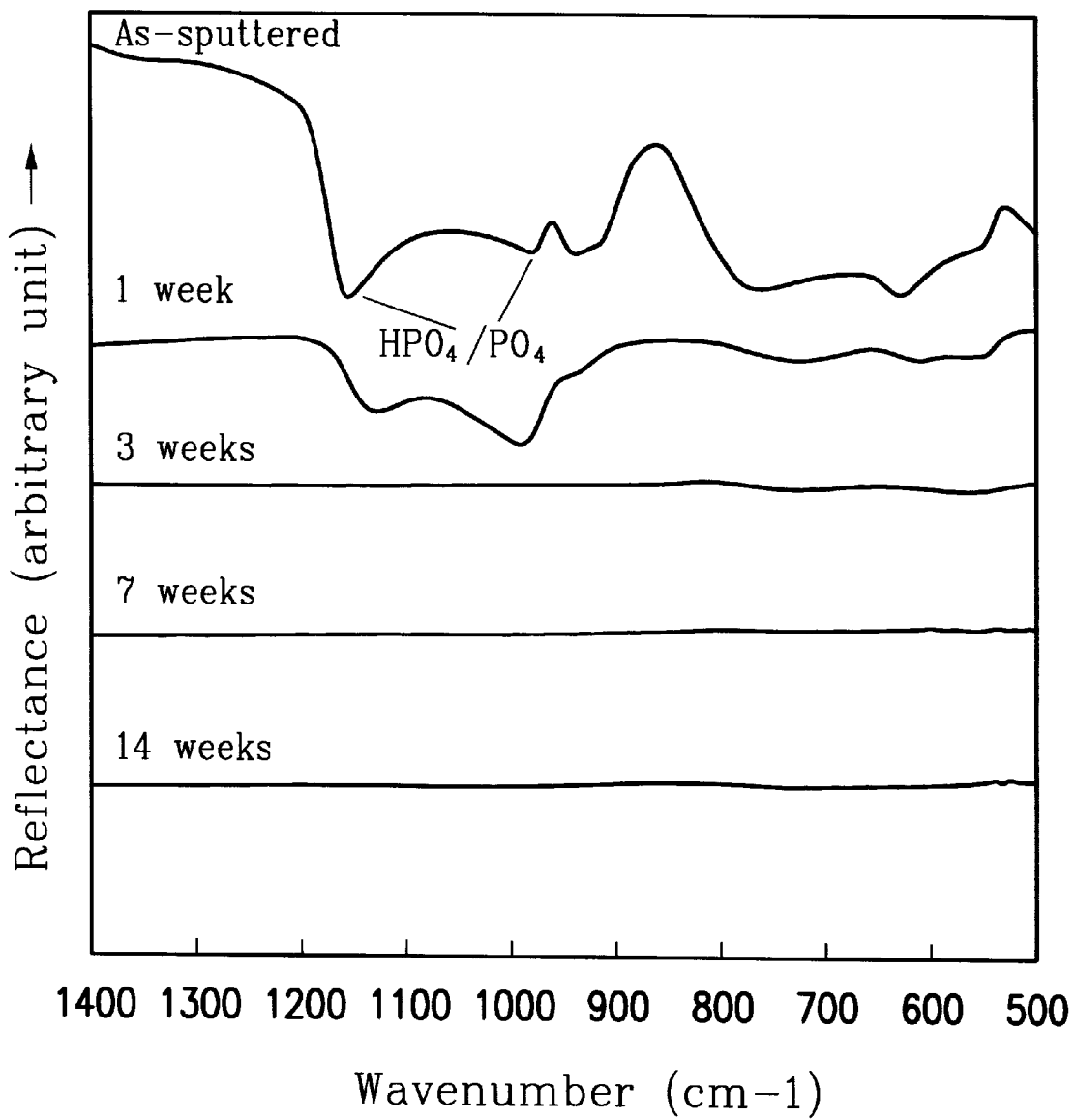
Figure 18:
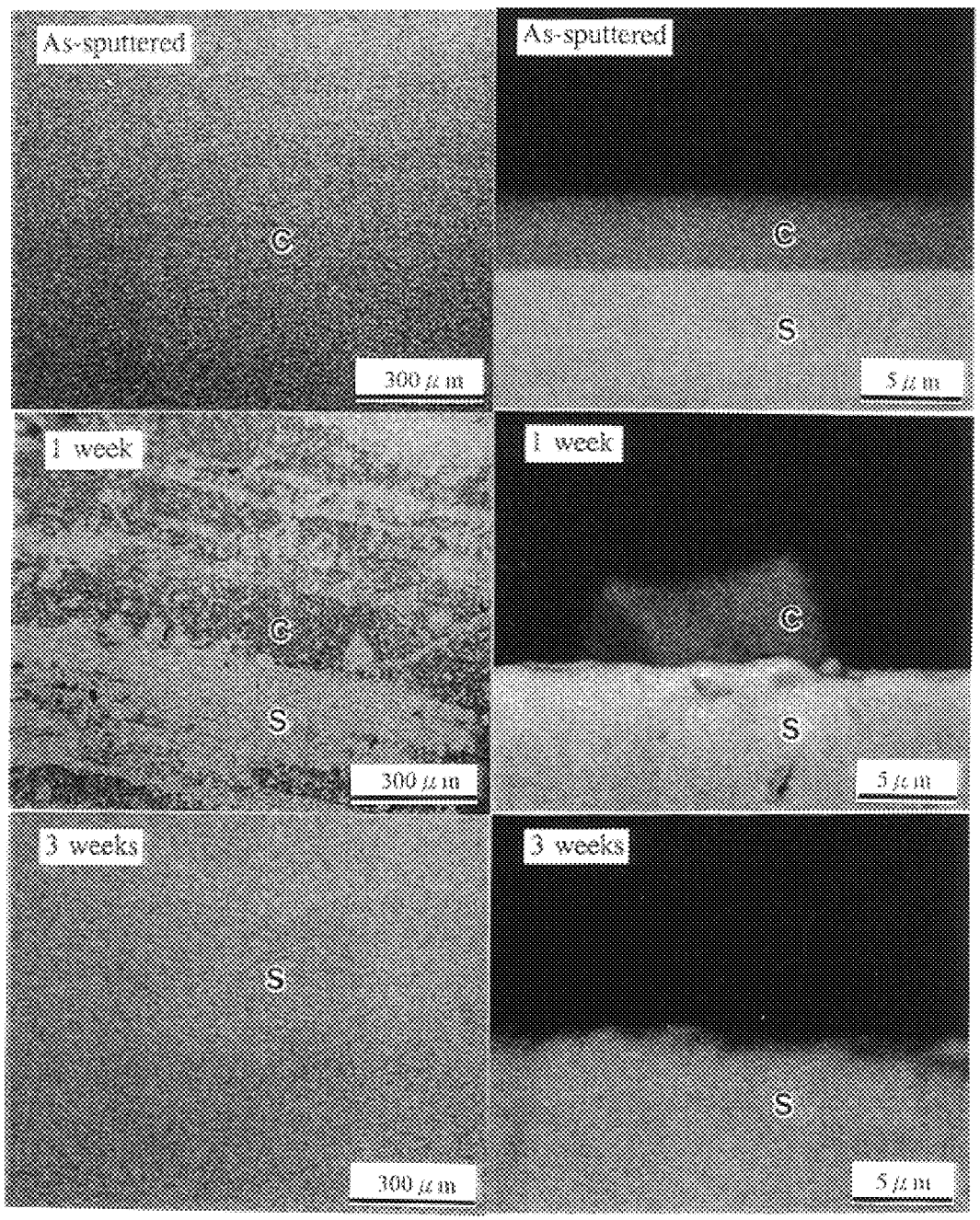
Figure 19:
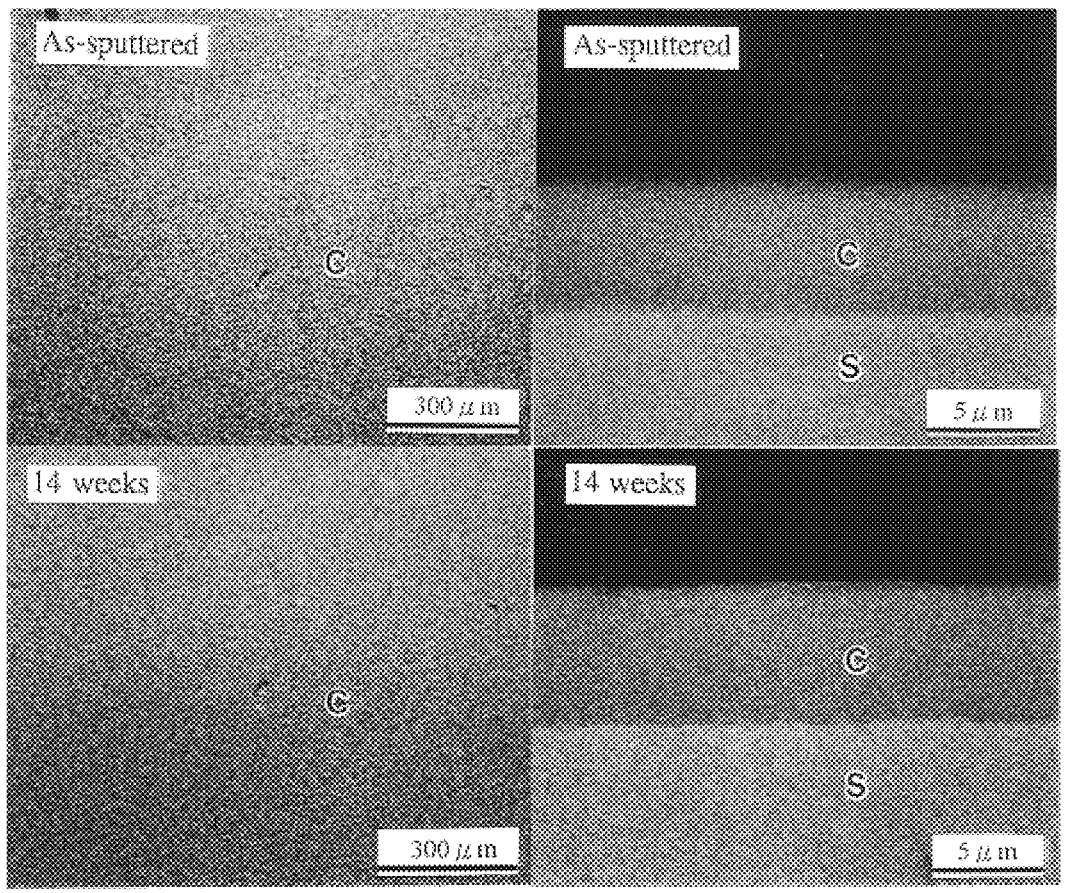
Figure 20:
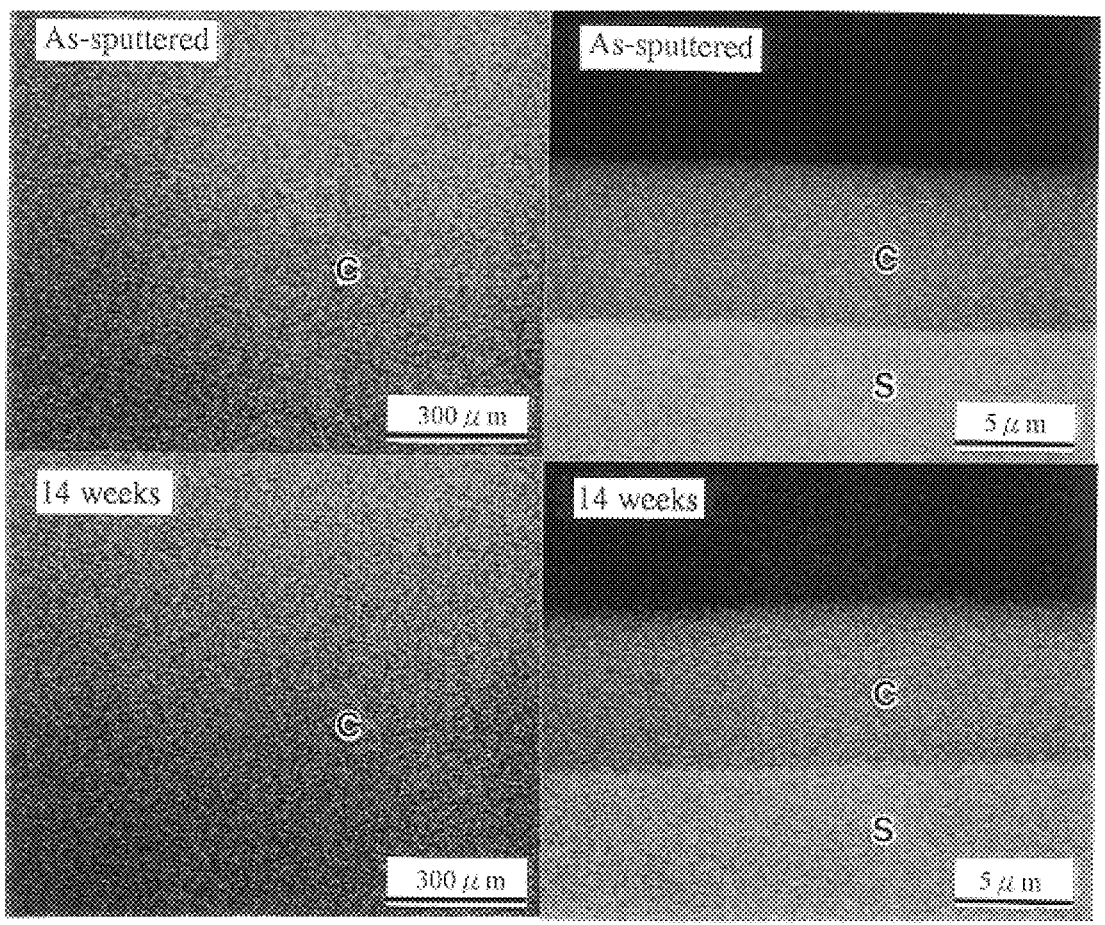
Figure 21:
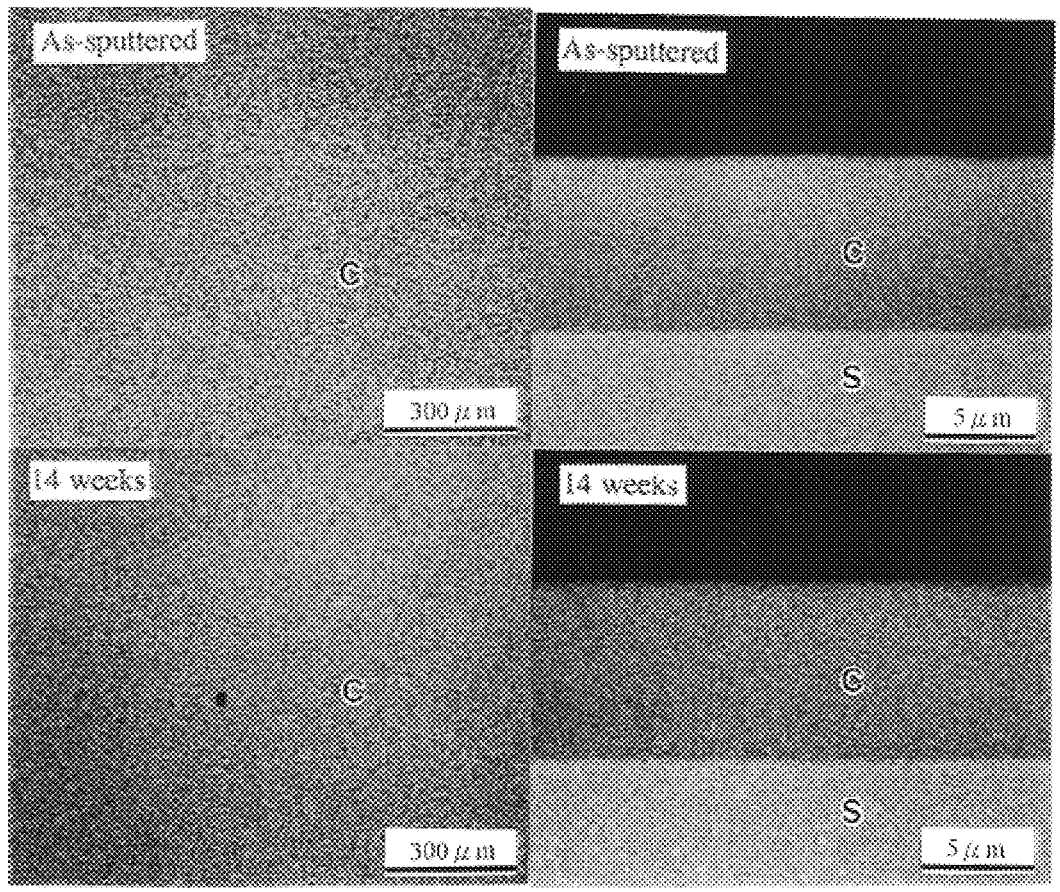
Figure 22:
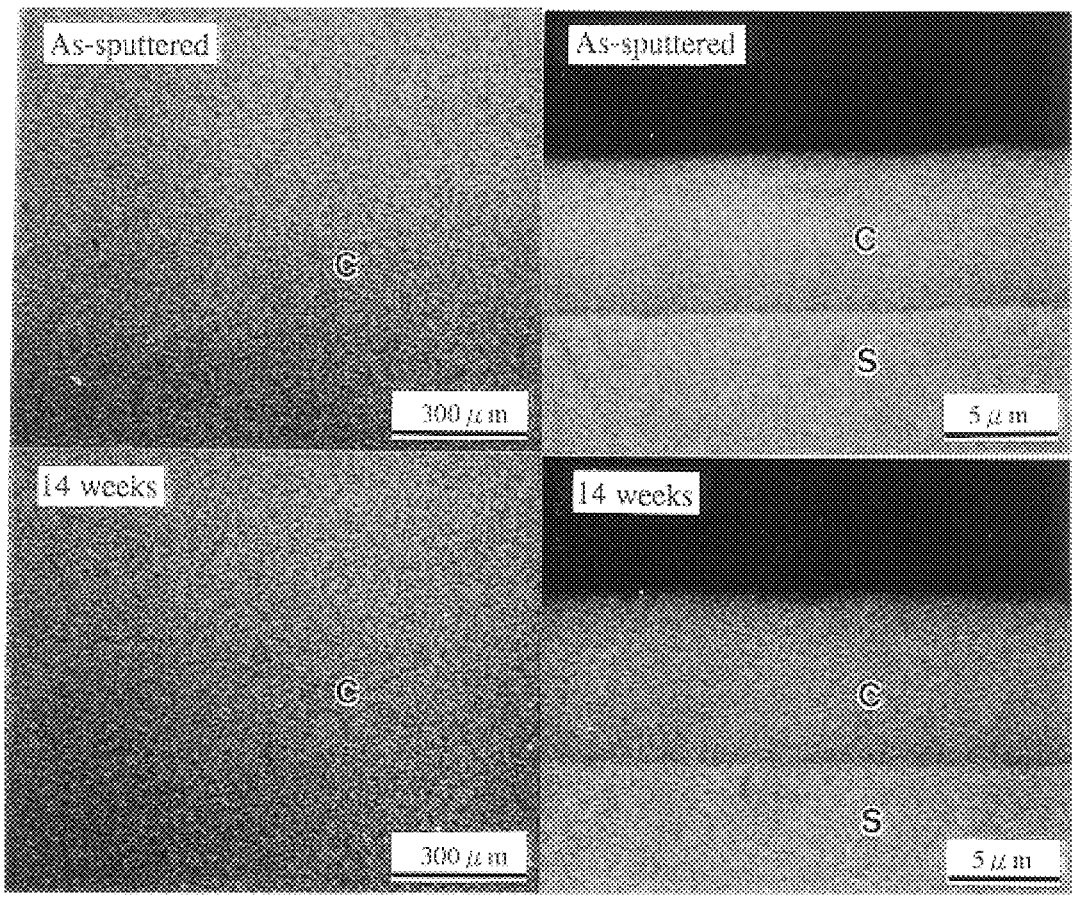
Figure 23:
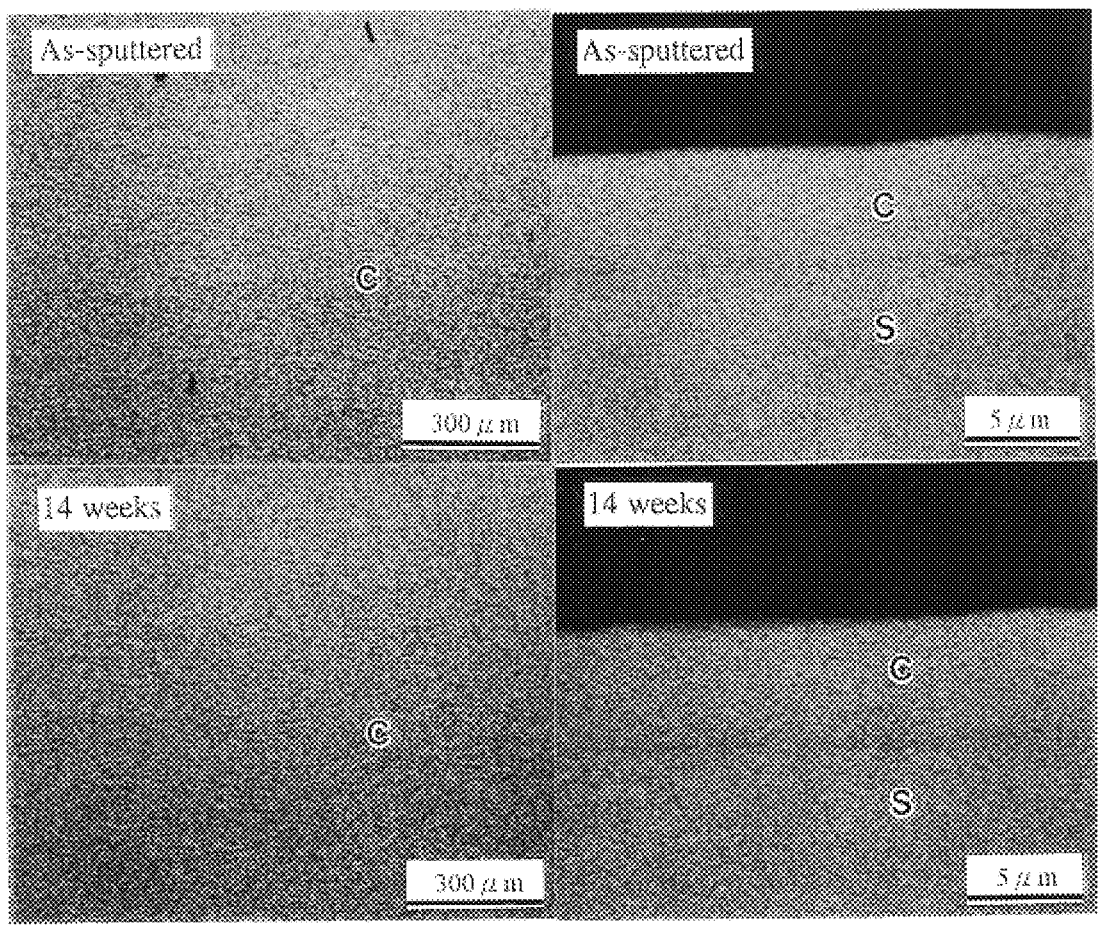
Figure 24:
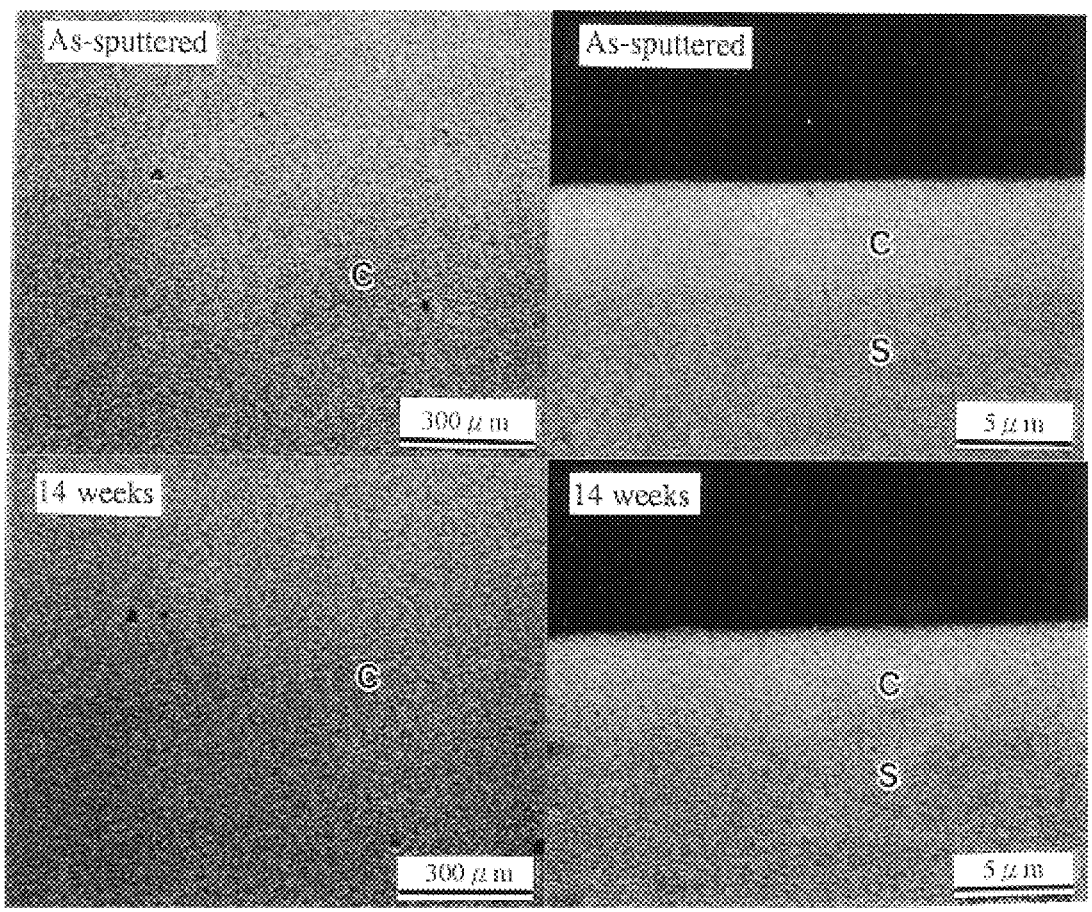

Even more severe degradation was observed in the immersed 95HA/5Ti coating. As shown in FIG. 18, the coating was severely cracked and spalled off the substrate when immersed for only 1 week. The 3-week specimen showed that entire coating was gone, confirming the earlier FTIR result (FIG. 10). As shown in FIG. 19, all coatings sputtered from targets comprising 10 vol % or more Ti appeared smooth, dense and well bonded to the substrate. The cross-sectional SEM micrographs showed that the contrast between coating and substrate decreased with increasing Ti content in target, indicating the degree in chemical similarity between coating and substrate increased with Ti content. When immersed in SBF, the coatings from targets comprising 10 vol % or more Ti appeared almost totally intact even after 14 weeks, again confirming the XRD and FTIR results.

Adhesion strength

Figure 25:
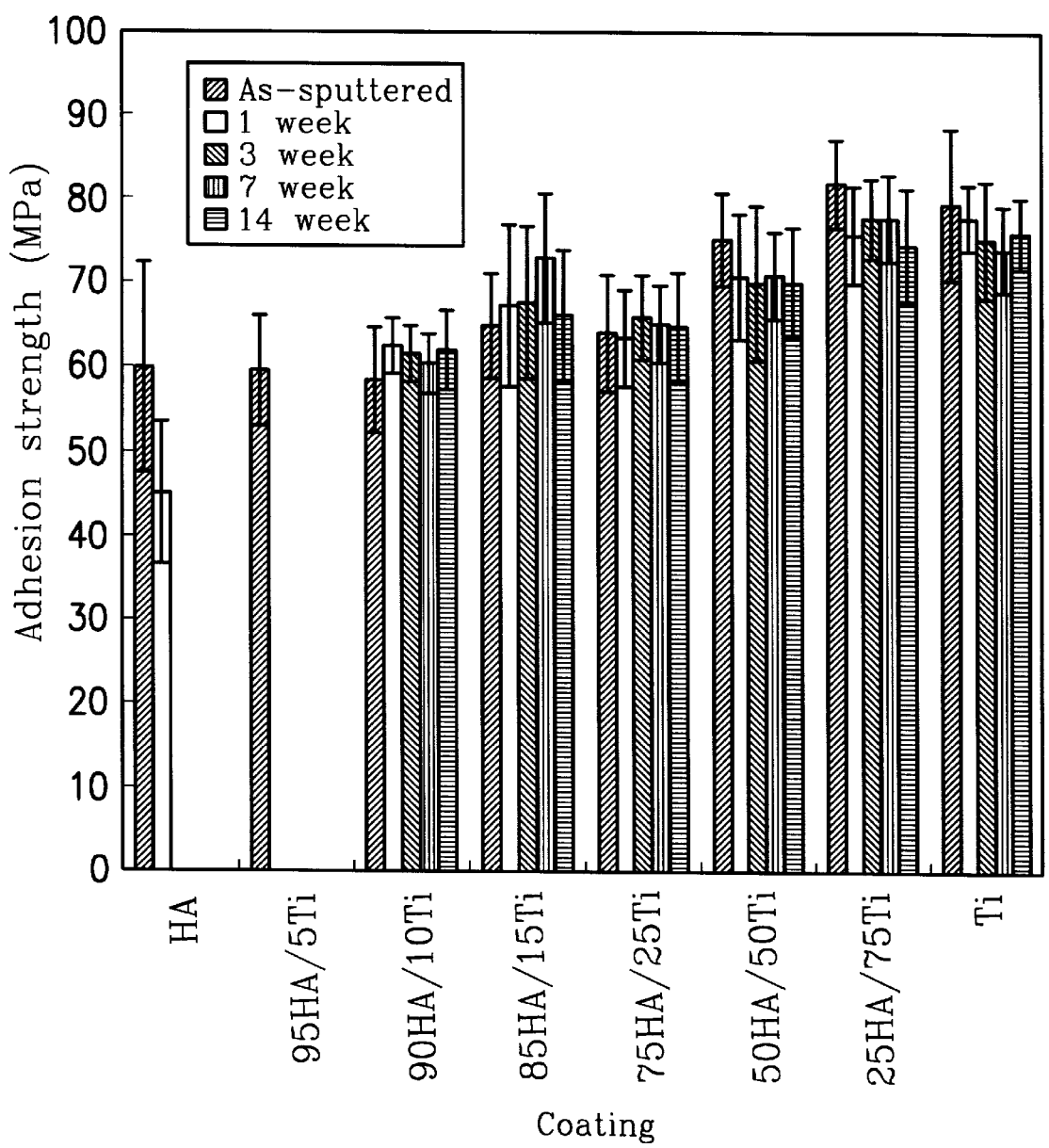
FIG. 25 illustrates the adhesion strengths for various as-sputtered and immersed coatings over different immersion times.

As indicated in FIG. 25, in general, the coatings with higher Ti contents had higher adhesion strengths. Even the lowest adhesion strengths (of monolithic HA, 95HA/5Ti and 90HA/10Ti coatings) of the series of as-sputtered coatings were as high as about 60 MPa. The highest adhesion strength (of 25HA/75Ti coating) was even higher than 80 MPa, that was about the maximum achievable using the present bonding resin in the pull-out test.

The variations in adhesion strength with immersion time of the series of coatings are also presented in FIG. 25. Four immersion times, 1, 3, 7 and 14 weeks, were selected for testing of the coatings sputtered from targets comprising 10 vol % or more Ti. For monolithic HA coating, only 1-week specimen was tested. For 95HA/5Ti coating, none of the immersed specimens was tested due to its severe delamination even in the 1-week specimen. As indicated in FIG. 25, after immersion for 1 week, the adhesion strength of monolithic HA coating largely declined from 59.9 MPa, the as-sputtered adhesion strength, down to 45.1 MPa. Even worse behavior was found in 95HA/5Ti coating immersed in SBF. As mentioned earlier, although the as-sputtered adhesion strength was quite high (59.5 MPa), the coating was largely disintegrated in a week of immersion.

The high adhesion strengths of the coatings sputtered from targets comprising more than 10 vol % Ti did not increase or decrease appreciably after immersion. The variations in adhesion strength within 14 weeks of immersion for all these coatings were within 10%. Except for the 90HA/10Ti coating, that had an adhesion strength comparable to that of as-sputtered monolithic HA coating, all the other coatings had adhesion strengths, as-sputtered or immersed, higher than that of monolithic HA coating.

Coating chemistry

Chemical distribution of three major elements, Ca, P and Ti, in the series of coatings was studied using SEM-EDS technique. The average Ca/Ti and P/Ti ratios of all coatings were listed in Table III. As can be seen in Table III, the Ca+P/Ti ratio of the coating decreased when the Ti/HA ratio of the composite target increased.

The XRD, FTIR, LVSEM and SEM-EDS results described above consistently indicate that the magnetron-sputtered, highly crystalline monolithic HA coating on Ti—6Al—4V substrate was highly dissolvable in SBF. The monolithic HA coating was largely delaminated in 3 weeks and entirely peeled off from substrate in 7 weeks. The immersion behavior was even worse for 95HA/5Ti coating, which severely spalled off substrate in only 1 week.

However, the amorphous-like coatings sputtered from targets comprising 10 vol % or more Ti appeared almost totally intact and their adhesion strengths, all higher than 60 MPa, did not change much (within 10%) even after 14 weeks of immersion.

The implant with coatings deposited from targets comprising roughly 10–50 vol % Ti and 90–50 vol % HA have the advantages in high and non-declining adhesion strength and high resistance to SBF attack, combined with higher bioactivity resulting from the large amounts of Ca+P dissolved in the coating. Therefore, they are suitable for application as dental implants, orthopedic prosthesis, and other kinds of medical implants.

While the invention has been described with reference to various illustrative embodiments, the description is not intended to be construed in a limiting sense. Various modifications of the illustrative embodiments, as well as other embodiments of the invention, will be apparent to those persons skilled in the art upon reference to this description. It is therefore contemplated that the appended claims will cover any such modifications or embodiments as may fall within the scope of the invention defined by the following claims and their equivalents.

TABLE III

Chemical Compositions of Coatings Determined by SEM-EDS

| | Target Composition | | | | | | | Coating Composition | | | | | |
|---|---|---|---|---|---|---|---|---|---|---|---|---|---|
| | | | Ca/Ti | | P/Ti | | (Ca + P)/Ti | | Ca/Ti | | P/Ti | | (Ca + P)/Ti | |
| Coating Code | HA:Ti vol. ratio | HA:Ti wt. ratio | at ratio | wt ratio | at ratio | wt ratio | at ratio | wt ratio | at ratio | wt ratio | at ratio | wt ratio | at ratio | wt ratio |
| HA | 100:0 | 100:0 | — | — | — | — | — | — | — | — | — | — | — | — |
| 95HA/5Ti | 95:5 | 13:1 | 59.7 | 50.0 | 32.6 | 21.1 | 92.4 | 71.2 | 4.7 | 4.0 | 2.4 | 1.5 | 7.1 | 5.5 |
| 90HA/10Ti | 90:10 | 6:1 | 28.3 | 23.7 | 15.4 | 10.0 | 43.7 | 33.6 | 2.8 | 2.3 | 1.0 | 0.7 | 3.8 | 3.0 |
| 85HA/15Ti | 85:15 | 4:1 | 12.9 | 10.9 | 7.3 | 4.7 | 20.2 | 15.6 | 1.8 | 1.5 | 0.6 | 0.4 | 2.3 | 1.8 |
| 75HA/25Ti | 75:25 | 2:1 | 6.1 | 5.1 | 3.5 | 2.3 | 9.7 | 7.3 | 0.9 | 0.8 | 0.1 | 0.1 | 1.1 | 0.9 |
| 50HA/50Ti | 50:50 | 2:3 | 1.7 | 1.4 | 0.9 | 0.6 | 2.6 | 1.9 | 0.3 | 0.3 | 0.2 | 0.1 | 0.5 | 0.4 |
| 25HA/75Ti | 25:75 | 2:9 | 0.5 | 0.4 | 0.3 | 0.2 | 0.7 | 0.6 | 0.1 | 0.1 | 0.1 | <0.1 | 0.2 | 0.1 |
| Ti | 0:100 | 0:100 | 0 | 0 | 0 | 0 | 0 | 0 | 0 | 0 | 0 | 0 | 0 | 0 |

What is claimed is:

1. A medical implant with a single non-dissolvable amorphous hydroxyapatite/titanium coating comprising:
   a substrate; and
   an amorphous HA/Ti surface coating on said substrate, wherein said HA/Ti surface coating has a weight ratio of Ca+P to Ti in the range of approximately 0.1–3.0.

2. The medical implant of claim 1, wherein the weight ratio of Ca+P to Ti in the surface coating is in the range of approximately 0.4–3.0.

3. The medical implant of claim 1, wherein the surface coating is less than approximately 10 μm thick.

4. The medical implant of claim 1, wherein the substrate is comprised of pure titanium.

5. The medical implant of claim 1, wherein the substrate is comprised of a titanium alloy.

6. The medical implant of claim 1, wherein the substrate is comprised of Ti—6Al—4V.

7. The medical implant of claim 1, wherein the surface coating is deposited onto the substrate from a composite target comprising 10–75% by volume of titanium and 90–25% by volume of hydroxyapatite.

8. The medical implant of claim 7, wherein the composite target comprises 10–50% by volume of titanium and 90–50% by volume of hydroxyapatite.

9. The medical implant of claim 8, wherein the composite target comprises 10% by volume of titanium and 90% by volume of hydroxyapatite.

10. The medical implant of claim 8, wherein the composite target comprises 15% by volume of titanium and 85% by volume of hydroxyapatite.

11. The medical implant of claim 8, wherein the composite target comprises 25% by volume of titanium and 75% by volume of hydroxyapatite.

12. The medical implant of claim 8, wherein the composite target comprises 50% by volume of titanium and 50% by volume of hydroxyapatite.

13. The medical implant of claim 7, wherein the hydroxyapatite component of the composite target is calcinated.

14. A medical implant comprising a substrate of pure titanium or a titanium alloy; and an amorphous coating on said substrate, wherein said amorphous coating consists essentially of amorphous hydroxyapatite and titanium.

* * * * *